(12) United States Patent
Shachar

(10) Patent No.: US 7,873,402 B2
(45) Date of Patent: *Jan. 18, 2011

(54) SYSTEM AND METHOD FOR RADAR-ASSISTED CATHETER GUIDANCE AND CONTROL

(75) Inventor: Yehoshua Shachar, Santa Monica, CA (US)

(73) Assignee: Magnetecs, Inc., Inglewood, CA (US)

( * ) Notice: Subject to any disclaimer, the term of this patent is extended or adjusted under 35 U.S.C. 154(b) by 472 days.

This patent is subject to a terminal disclaimer.

(21) Appl. No.: 11/869,668

(22) Filed: Oct. 9, 2007

(65) Prior Publication Data

US 2008/0027313 A1 Jan. 31, 2008

Related U.S. Application Data

(63) Continuation of application No. 10/690,472, filed on Oct. 20, 2003, now Pat. No. 7,280,863.

(51) Int. Cl.
*A61B 5/05* (2006.01)
(52) U.S. Cl. .................. 600/424; 600/114; 600/117; 600/118; 600/173; 600/420
(58) Field of Classification Search .............. 600/114, 600/117, 118, 173, 420, 424
See application file for complete search history.

(56) References Cited

U.S. PATENT DOCUMENTS 3,043,309 A 7/1962 McCarthy (Continued)

FOREIGN PATENT DOCUMENTS

DE 102005045073 A1 3/2007

EP 0147082 A2 7/1985

(Continued)

OTHER PUBLICATIONS

Office Action dated Feb. 5, 2008 from Related U.S. Appl. No. 10/621,196.

(Continued)

*Primary Examiner*—Brian Casler
*Assistant Examiner*—James Kish
(74) *Attorney, Agent, or Firm*—Knobbe, Martens, Olson & Bear, LLP

(57) ABSTRACT

A Catheter Guidance Control and Imaging (CGCI) system whereby a magnetic tip attached to a surgical tool is detected, displayed and influenced positionally so as to allow diagnostic and therapeutic procedures to be performed is described. The tools that can be so equipped include catheters, guidewires, and secondary tools such as lasers and balloons. The magnetic tip performs two functions. First, it allows the position and orientation of the tip to be determined by using a radar system such as, for example, a radar range finder or radar imaging system. Incorporating the radar system allows the CGCI apparatus to detect accurately the position, orientation and rotation of the surgical tool embedded in a patient during surgery. In one embodiment, the image generated by the radar is displayed with the operating room imagery equipment such as, for example, X-ray, Fluoroscopy, Ultrasound, MRI, CAT-Scan, PET-Scan, etc. In one embodiment, the image is synchronized with the aid of fiduciary markers located by a 6-Degrees of Freedom (6-DOF) sensor. The CGCI apparatus combined with the radar and the 6-DOF sensor allows the tool tip to be pulled, pushed, turned, and forcefully held in the desired position by applying an appropriate magnetic field external to the patient's body. A virtual representation of the magnetic tip serves as an operator control. This control possesses a one-to-one positional relationship with the magnetic tip inside the patient's body. Additionally, this control provides tactile feedback to the operator's hands in the appropriate axis or axes if the magnetic tip encounters an obstacle. The output of this control combined with the magnetic tip position and orientation feedback allows a servo system to control the external magnetic field.

10 Claims, 20 Drawing Sheets

U.S. PATENT DOCUMENTS

| | | | |
|---|---|---|---|
| 3,358,676 A | 12/1967 | Frei et al. | |
| 3,622,869 A | 11/1971 | Golay | |
| 3,628,527 A | 12/1971 | West | |
| 3,746,937 A | 7/1973 | Koike | |
| 3,961,632 A | 6/1976 | Moossun | |
| 4,063,561 A | 12/1977 | McKenna | |
| 4,096,862 A | 6/1978 | DeLuca | |
| 4,162,679 A | 7/1979 | Reenstierna | |
| 4,173,228 A | 11/1979 | Van Steenwyk et al. | |
| 4,244,362 A | 1/1981 | Anderson | |
| 4,249,536 A | 2/1981 | Vega | |
| 4,270,252 A | 6/1981 | Harrison et al. | |
| 4,292,961 A | 10/1981 | Kawashima | |
| 4,354,501 A | 10/1982 | Colley et al. | |
| 4,392,634 A | 7/1983 | Kita | |
| 4,671,287 A | 6/1987 | Fiddian-Green | |
| 4,727,344 A | 2/1988 | Koga et al. | |
| 4,735,211 A | 4/1988 | Takasugi | |
| 4,809,713 A | 3/1989 | Grayzel | |
| 4,869,247 A | 9/1989 | Howard, III et al. | |
| 4,943,770 A | 7/1990 | Ashley-Rollman et al. | |
| 4,984,581 A | 1/1991 | Stice | |
| 4,985,015 A | 1/1991 | Obermann et al. | |
| 5,063,935 A | 11/1991 | Gambale | |
| 5,083,562 A | 1/1992 | de Coriolis et al. | |
| 5,090,956 A | 2/1992 | McCoy | |
| 5,125,888 A | 6/1992 | Howard et al. | |
| 5,167,626 A | 12/1992 | Casper et al. | |
| 5,209,234 A | 5/1993 | LaRocca | |
| 5,226,847 A | 7/1993 | Thomas et al. | |
| 5,249,163 A | 9/1993 | Erickson | |
| 5,255,680 A | 10/1993 | Darrow et al. | |
| 5,257,636 A | 11/1993 | White | |
| 5,269,759 A | 12/1993 | Hernandez et al. | |
| 5,353,807 A | 10/1994 | DeMarco | |
| 5,377,678 A | 1/1995 | Dumoulin et al. | |
| 5,396,902 A | 3/1995 | Brennen et al. | |
| 5,492,131 A | 2/1996 | Galel | |
| 5,546,948 A | 8/1996 | Hamm et al. | |
| 5,550,469 A | 8/1996 | Tanabe et al. | |
| 5,558,091 A | 9/1996 | Acker et al. | |
| 5,573,012 A | 11/1996 | McEwan | |
| 5,588,442 A | 12/1996 | Scovil et al. | |
| 5,624,430 A | 4/1997 | Eton et al. | |
| 5,645,065 A | 7/1997 | Shapiro et al. | |
| 5,650,725 A | 7/1997 | Powell et al. | |
| 5,650,864 A | 7/1997 | Tseng et al. | |
| 5,654,864 A | 8/1997 | Ritter et al. | |
| 5,656,030 A | 8/1997 | Hunjan et al. | |
| 5,681,260 A | 10/1997 | Ueda et al. | |
| 5,683,384 A | 11/1997 | Gough et al. | |
| 5,702,433 A | 12/1997 | Taylor et al. | |
| 5,704,897 A | 1/1998 | Truppe | |
| 5,709,661 A | 1/1998 | Van Egmond et al. | |
| 5,711,299 A | 1/1998 | Manwaring et al. | |
| 5,769,843 A | 6/1998 | Abela et al. | |
| 5,775,322 A | 7/1998 | Silverstein et al. | |
| 5,779,694 A | 7/1998 | Howard et al. | |
| 5,808,665 A * | 9/1998 | Green | 348/65 |
| 5,821,920 A | 10/1998 | Rosenberg et al. | |
| 5,843,153 A | 12/1998 | Johnston et al. | |
| 5,844,140 A | 12/1998 | Seale | |
| 5,904,691 A | 5/1999 | Barnett et al. | |
| 5,931,818 A | 8/1999 | Werp et al. | |
| 5,971,976 A | 10/1999 | Wang et al. | |
| 6,014,580 A * | 1/2000 | Blume et al. | 600/424 |
| 6,015,414 A | 1/2000 | Werp et al. | |
| 6,038,488 A | 3/2000 | Barnes et al. | |
| 6,104,944 A | 8/2000 | Martinelli | |
| 6,122,538 A | 9/2000 | Sliwa et al. | |
| 6,128,174 A | 10/2000 | Ritter et al. | |
| 6,129,668 A | 10/2000 | Haynor et al. | |
| 6,148,823 A | 11/2000 | Hastings | |
| 6,152,933 A | 11/2000 | Werp et al. | |
| 6,157,853 A | 12/2000 | Blume et al. | |
| 6,200,312 B1 | 3/2001 | Zikorous et al. | |
| 6,241,671 B1 | 6/2001 | Ritter et al. | |
| 6,292,678 B1 | 9/2001 | Hall et al. | |
| 6,295,466 B1 | 9/2001 | Ishikawa et al. | |
| 6,296,604 B1 | 10/2001 | Garibaldi et al. | |
| 6,298,257 B1 | 10/2001 | Hall et al. | |
| 6,304,768 B1 | 10/2001 | Blume et al. | |
| 6,311,082 B1 | 10/2001 | Creighton, IV et al. | |
| 6,314,312 B1 | 11/2001 | Wessels et al. | |
| 6,315,709 B1 | 11/2001 | Garibaldi et al. | |
| 6,330,467 B1 | 12/2001 | Creighton, IV et al. | |
| 6,352,363 B1 | 3/2002 | Munger et al. | |
| 6,364,823 B1 | 4/2002 | Garibaldi et al. | |
| 6,375,606 B1 | 4/2002 | Garibaldi et al. | |
| 6,381,485 B1 | 4/2002 | Hunter et al. | |
| 6,385,472 B1 | 5/2002 | Hall et al. | |
| 6,401,723 B1 | 6/2002 | Garibaldi et al. | |
| 6,428,551 B1 | 8/2002 | Hall et al. | |
| 6,454,776 B1 | 9/2002 | Tajima et al. | |
| 6,459,924 B1 | 10/2002 | Creighton, IV et al. | |
| 6,459,926 B1 | 10/2002 | Nowlin et al. | |
| 6,475,223 B1 | 11/2002 | Werp et al. | |
| 6,505,062 B1 | 1/2003 | Ritter et al. | |
| 6,507,751 B2 | 1/2003 | Blume et al. | |
| 6,522,909 B1 | 2/2003 | Garibaldi et al. | |
| 6,524,303 B1 | 2/2003 | Garibaldi | |
| 6,529,761 B2 | 3/2003 | Creighton, IV et al. | |
| 6,537,196 B1 | 3/2003 | Creighton, IV et al. | |
| 6,562,019 B1 | 5/2003 | Sell | |
| 6,575,977 B1 | 6/2003 | Michelson | |
| 6,587,709 B2 | 7/2003 | Solf et al. | |
| 6,594,517 B1 | 7/2003 | Nevo | |
| 6,630,879 B1 | 10/2003 | Creighton, IV et al. | |
| 6,662,034 B2 | 12/2003 | Segner et al. | |
| 6,667,660 B2 | 12/2003 | Schrodinger et al. | |
| 6,669,693 B2 | 12/2003 | Friedman | |
| 6,677,752 B1 | 1/2004 | Creighton, IV et al. | |
| 6,702,804 B1 | 3/2004 | Ritter et al. | |
| 6,704,694 B1 | 3/2004 | Basdogan et al. | |
| 6,726,675 B1 | 4/2004 | Beyar | |
| 6,733,511 B2 | 5/2004 | Hall et al. | |
| 6,740,103 B2 | 5/2004 | Hall et al. | |
| 6,755,816 B2 | 6/2004 | Ritter et al. | |
| 6,776,165 B2 | 8/2004 | Jin | |
| 6,786,219 B2 | 9/2004 | Garibaldi et al. | |
| 6,817,364 B2 | 11/2004 | Garibaldi et al. | |
| 6,834,201 B2 | 12/2004 | Gillies et al. | |
| 6,853,965 B2 | 2/2005 | Massie et al. | |
| 6,902,528 B1 | 6/2005 | Garibaldi | |
| 6,914,552 B1 * | 7/2005 | McEwan | 342/22 |
| 6,960,847 B2 | 11/2005 | Suzuki et al. | |
| 7,280,863 B2 | 10/2007 | Shachar | |
| 7,316,700 B2 | 1/2008 | Alden et al. | |
| 7,341,063 B2 | 3/2008 | Garbibaldi et al. | |
| 7,346,379 B2 | 3/2008 | Eng et al. | |
| 7,495,537 B2 | 2/2009 | Tunay | |
| 7,543,239 B2 | 6/2009 | Viswanathan et al. | |
| 2001/0004215 A1 | 6/2001 | Kubota et al. | |
| 2001/0021805 A1 * | 9/2001 | Blume et al. | 600/407 |
| 2002/0022777 A1 | 2/2002 | Crieghton, IV et al. | |
| 2002/0055674 A1 | 5/2002 | Ben-Haim et al. | |
| 2002/0058866 A1 | 5/2002 | Eng et al. | |
| 2002/0103430 A1 | 8/2002 | Hastings et al. | |
| 2003/0205941 A1 | 11/2003 | Suzuki et al. | |
| 2003/0233112 A1 | 12/2003 | Alden et al. | |
| 2004/0019447 A1 | 1/2004 | Shachar | |
| 2005/0004449 A1 | 1/2005 | Mitschke et al. | |
| 2005/0096589 A1 | 5/2005 | Shachar | |
| 2005/0256521 A1 | 11/2005 | Kozel | |

| | | | |
|---|---|---|---|
| 2006/0114088 A1 | 6/2006 | Shachar | |
| 2006/0116633 A1 | 6/2006 | Shachar | |
| 2006/0116634 A1 | 6/2006 | Shachar | |
| 2006/0217697 A1 | 9/2006 | Lau et al. | |
| 2007/0016006 A1 | 1/2007 | Shachar | |
| 2007/0062547 A1 | 3/2007 | Pappone | |
| 2007/0197891 A1 | 8/2007 | Shachar | |
| 2008/0027313 A1 | 1/2008 | Shachar | |
| 2008/0249395 A1 | 10/2008 | Shachar et al. | |
| 2008/0297287 A1 | 12/2008 | Shachar et al. | |
| 2009/0248014 A1 | 10/2009 | Shachar et al. | |
| 2009/0253985 A1 | 10/2009 | Shachar et al. | |
| 2009/0275828 A1 | 11/2009 | Shachar et al. | |

FOREIGN PATENT DOCUMENTS

| | | |
|---|---|---|
| EP | 1 059 067 | 12/2000 |
| EP | 1059067 A1 | 12/2000 |
| EP | 1 115 327 | 7/2001 |
| GB | 2367803 A | 4/2002 |
| JP | 2000-509316 | 7/2000 |
| JP | 2001-448 | 1/2001 |
| JP | 2001-509038 | 7/2001 |
| JP | 2001-514040 | 9/2001 |
| WO | WO 95-01757 A1 | 1/1995 |
| WO | WO 97-29803 A1 | 8/1997 |
| WO | WO 98-35720 A2 | 8/1998 |
| WO | WO 99-11189 A1 | 3/1999 |
| WO | WO 99-23934 A2 | 5/1999 |
| WO | WO 00-07641 A | 2/2000 |
| WO | WO 02-19908 A | 3/2002 |
| WO | WO 02-34131 A1 | 5/2002 |
| WO | WO 02-094115 A2 | 11/2002 |
| WO | WO 02-094115 A3 | 11/2002 |
| WO | WO 2004-006795 A1 | 1/2004 |
| WO | WO 2005-042053 A2 | 5/2005 |
| WO | WO 2005-042053 A3 | 5/2005 |
| WO | WO 2005-112813 A1 | 12/2005 |
| WO | WO 2007-100559 A2 | 9/2007 |

OTHER PUBLICATIONS

Office Action dated Dec. 2, 2008 from Related U.S. Appl. No. 10/621,196.
Office Action dated Jan. 29, 2009 from Related U.S. Appl. No. 11/331,781.
Office Action dated Feb. 25, 2009 from Related U.S. Appl. No. 11/331,944.
Office Action dated Apr. 28, 2009 from Related U.S. Appl. No. 11/331,485.
Office Action dated May 6, 2009 from Related U.S. Appl. No. 11/362,542.
International Search Report from PCT/US2009/039659, Jul. 6, 2009, 4 pages.
Office Action dated Jul. 15, 2009 from Related U.S. Appl. No. 11/331,485.
Office Action dated Aug. 25, 2009 from Related U.S. Appl. No. 10/621,196.
Office Action dated Jul. 13, 2009 from Related U.S. Appl. No. 11/362,542.
Office Action dated Jul. 10, 2008 from Related U.S. Appl. No. 10/621,196.
Office Action dated Jun. 18, 2008 from Related U.S. Appl. No. 11/331,485.
Office Action dated Aug. 8, 2008 from Related U.S. Appl. No. 11/140,475.
International Search Report from PCT/US2008/060525, Oct. 31, 2008, 6 pages.
Office Action dated Feb. 22, 2006 from Related U.S. Appl. No. 10/621,196.
Office Action dated Nov. 14, 2006 from Related U.S. Appl. No. 10/621,196.
Office Action dated Apr. 18, 2007 from Related U.S. Appl. No. 10/621,196.
Office Action dated Sep. 10, 2007 from Related U.S. Appl. No. 10/621,196.
Advisory Action dated Nov. 6, 2007 from Related U.S. Appl. No. 10/621,196.
Office Action dated May 18, 2006 from Related U.S. Appl. No. 10/690,472.
Office Action dated Jan. 30, 2007 from Related U.S. Appl. No. 10/690,472.
Notice of Allowance dated Aug. 6, 2007 from Related U.S. Appl. No. 10/690,472.
International Search Report from PCT/US2007/004416, Aug. 24, 2007, 5 pages.
Bergveld, Piet, "Development, Operation, and Application of the Ion-Sensitive Field-Effect Transistor as a Tool for Electrophysiology", IEEE Transactions on Biomedical Engineering, vol. BME-19, No. 5, Sep. 1972, 10 pages.
Fink et al.,"An Optically Switched PS-Radar for Pictorial Representation of Object Structures in Human Tissue," Experimentelle Technik Der Physik, vol. 38, No. 3, 1990, pp. 197-206, 10 pages.
International Search Report from PCT/US2008/056277, Nov. 18, 2008, 5 pages.
Supplementary Partial Search Report from 04795885.5, Nov. 18, 2008, 5 pages.
Extended European Search Report from 09005296.0, Aug. 19, 2009, 3 pages.
Faddis et al., "Novel, Magnetically Guided Catheter for Endocardial Mapping and Radiofrequency Catheter Ablation," Journal of the American Heart Association, Nov. 11, 2002.
Fink et al., "An Optically Switched PS-Radar for Pictorial Representation of Object Structures in Human Tissue," Experimentelle Technik De Physik, vol. 38, No. 3, 1990, pp. 197-206, 10 pages.
International Search Report from PCT Application No. PCT/US03/22122; 9 pages.
International Search Report from PCT/US2008/056277, Nov. 18, 2008, 7 pages.
Ishiyama, K.; Sendoh, M.; Arai, K.I.; Magnetic micromachines for medical applications. Journal of Magnetism and Magnetic Materials. 2002; vol. 242; pp. 41-46.
Ritter, J.A.; Ebner, A.D.;Daniel, K.D.; Stewart, K.L.; Application of high gradient magnetic separation principles to magnetic drug targeting. Journal of Magnetism and Magnetic Materials. 2004; vol. 280; pp. 184-201.
Supplementary Partial European Search Report from 04795885.5, Nov. 18, 2008, 5 pages.
Totsu, K.; Haga, Y.; Esashi, M.; Three-axis magneto-impedance effect sensor system for detecting position and orientation of catheter tip. Sensors and Actuators. 2004; Issue A 111; pp. 304-309.

* cited by examiner

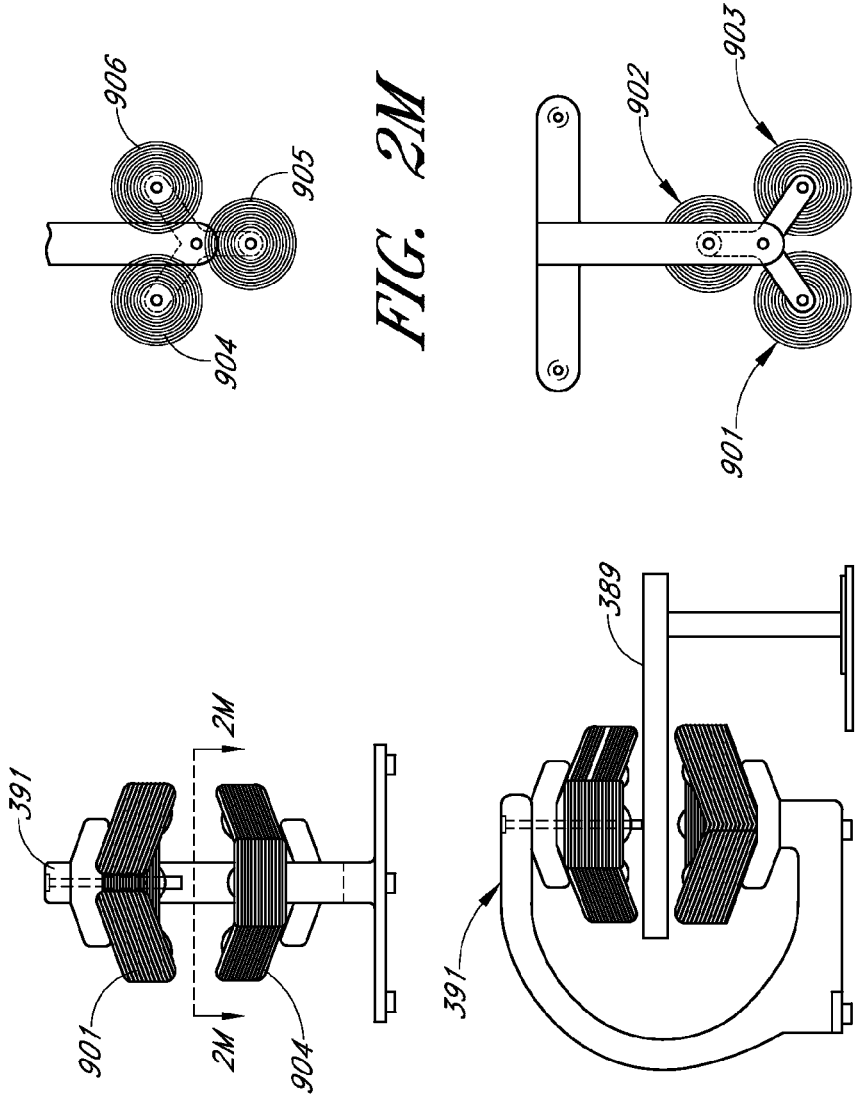

$$[B_x \ B_y \ B_z] = \begin{bmatrix} 1 & 0 & 0 \\ 0 & 1 & 0 \\ 0 & 0 & 1 \end{bmatrix} [V_{ix} \ V_{iy} \ V_{iz}]$$

*FIG. 2D*

$$[B_x \ B_y \ B_z] = \begin{bmatrix} C_{11} & C_{12} & C_{13} \\ C_{21} & C_{22} & C_{23} \\ C_{31} & C_{32} & C_{33} \end{bmatrix} [I_1 \ I_2 \ I_3]$$

*FIG. 2E*

$$[B_x \ B_y \ B_z] = \begin{bmatrix} R_{11} & R_{12} & R_{13} \\ R_{21} & R_{22} & R_{23} \\ R_{31} & R_{32} & R_{33} \end{bmatrix} [I_1 \ I_2 \ I_3]$$

*FIG. 2F*

$$[B_x \ B_y \ B_z] = \begin{bmatrix} R_{11} & R_{12} & R_{13} \\ R_{21} & R_{22} & R_{23} \\ R_{31} & R_{32} & R_{33} \end{bmatrix} \begin{bmatrix} C_{11} & C_{12} & C_{13} \\ C_{21} & C_{22} & C_{23} \\ C_{31} & C_{32} & C_{33} \end{bmatrix} [V_{ix} \ V_{iy} \ V_{iz}]$$

*FIG. 2G*

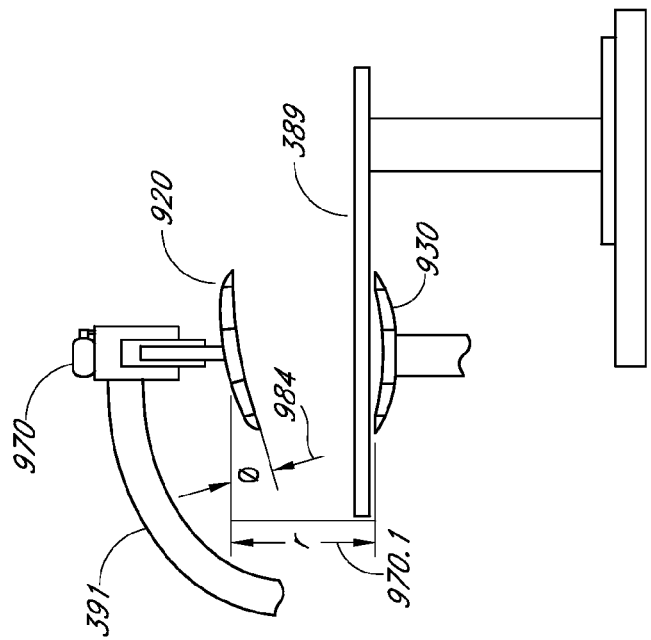
FIG. 2I
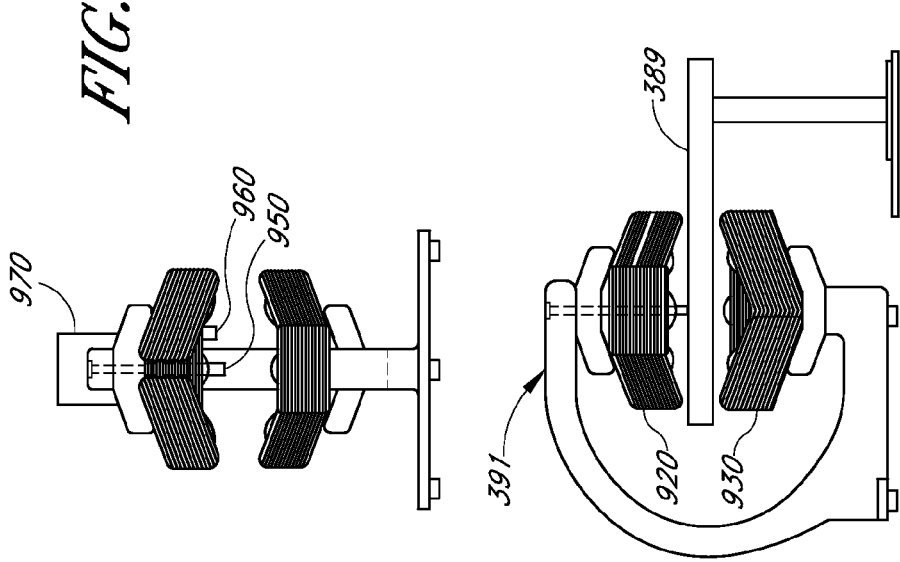
FIG. 2J
FIG. 2K

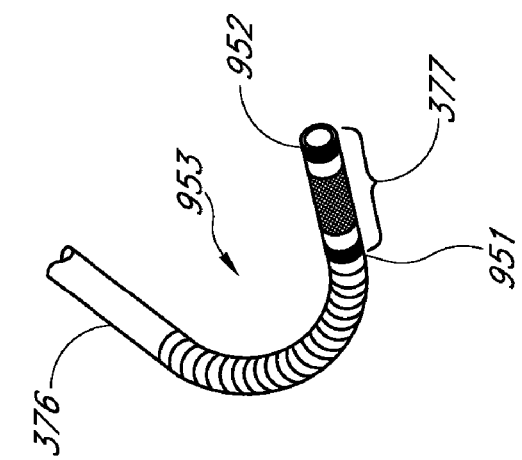
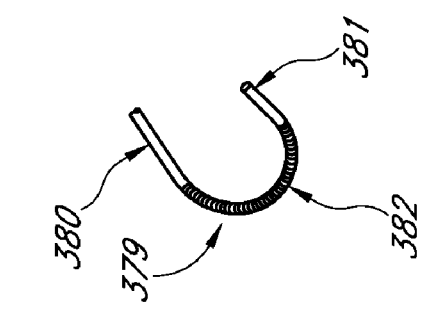
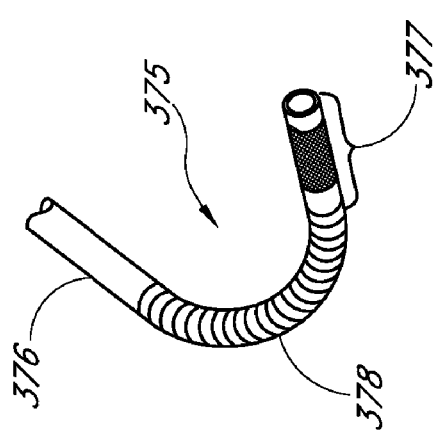
FIG. 6B
FIG. 6A
FIG. 6

SYSTEM AND METHOD FOR RADAR-ASSISTED CATHETER GUIDANCE AND CONTROL

REFERENCE TO RELATED APPLICATIONS

The present application is a continuation of application Ser. No. 10/690,472, filed Oct. 20, 2003, titled "SYSTEM AND METHOD FOR RADAR-ASSISTED CATHETER GUIDANCE AND CONTROL," the disclosure of which is incorporated herein by reference in its entirety.

BACKGROUND

1. Field of the Invention

The present invention relates to systems and techniques for guiding steering and advancing invasive medical devices such as catheter and catheter-type devices in a patient while using a radar system to determine the location of the catheter within the patient.

2. Description of the Related Art

Catheterization is typically performed by inserting an invasive device into an incision or a body orifice. Secondary tools such as guidewires and balloons are often advanced along the catheter to the area where the medical procedure is to be performed. These procedures rely on manually advancing the distal end of the invasive device by pushing, rotating, or otherwise manipulating the proximal end that remains outside of the body. Real-time X-ray imaging is a common method for determining the position of the distal end of the invasive device during the procedure. The manipulation continues until the distal end reaches the destination area where the diagnostic or therapeutic procedure is to be performed. This technique requires great skills on the part of the surgeon/operator. Such skill can only be achieved after a protracted training period and extended practice. A high degree of manual dexterity is also required.

Because of the difficulty involved in advancing a catheter into a desired location in the body, many diagnostic and therapeutic procedures often employ a guidewire. The guidewire is first advanced into the heart or the artery and serves as a track and guide for a specific catheter. For example, this technique is used to advance a catheter into the left ventricle and is especially important when studying aortic stenosis. Crossing the narrowed valve orifice is a challenge to the operator. Similarly, a guidewire is often manipulated into a blocked coronary artery and across the obstructive plaque. A therapeutic catheter, carrying, for example a balloon, a laser, a stent, etc., is advanced over the guidewire, and placed at the site of the plaque. The narrowed site is then opened by inflating a balloon, operating a laser beam, or placing a stent. On occasions, the artery is torturous and severely narrowed and the plaque is irregular, calcified, or even totally occluding the artery. In these situations the placement of a guidewire beyond the narrowed site is very difficult and many times unsuccessful.

Therefore, there is a substantial and unsatisfied need for an apparatus and method for guiding, steering, advancing and locating the position of invasive devices and for accurately controlling their position; for providing three dimensional imaging; and for minimizing the use of X-rays or other ionizing-type radiation

SUMMARY

The present invention solves these and other problems by providing a magnetic catheter guidance and control apparatus that requires less training and less skill than prior art systems. In one embodiment, a radar system is used to determine the location of the distal end of the catheter inside the body, thus minimizing or eliminating the use of ionizing radiation such as X-rays. Alternatively, the catheter guidance system can be used in combination with an X-ray system (or other imaging system) to provide additional imagery to the operator. Moreover, the magnetic system used in the magnetic catheter guidance system can also be used to locate the catheter tip to provide location feedback to the operator and the control system. In one embodiment, a magnetic field source is used to create a magnetic field of sufficient strength and orientation to move a magnetically-responsive catheter tip in a desired direction by a desired amount.

One embodiment includes a catheter and a guidance and control apparatus that can accurately, and with relative ease, allow the surgeon/operator to position the catheter tip inside a patient's body. The catheter guidance and control apparatus can maintain the catheter tip in the correct position. One embodiment includes a catheter and a guidance and control apparatus that can steer the distal end of the catheter through arteries and forcefully advance it through plaque or other obstructions. One embodiment includes a catheter guidance and control apparatus that displays the catheter tip location with significantly reduced X-ray exposure to the patient and staff. One embodiment includes a catheter guidance and control apparatus that is more intuitive and simpler to use, that displays the catheter tip location in three dimensions, that applies force at the catheter tip to pull, push, turn, or hold the tip as desired, and that is capable of producing a vibratory or pulsating motion of the tip with adjustable frequency and amplitude to aid in advancing the tip through plaque or other obstructions. One embodiment provides tactile feedback at the operator control to indicate an obstruction encountered by the tip.

In one embodiment, the catheter Guidance Control and Imaging (GCI) system allows a surgeon to advance, accurately position a catheter, and to view the catheter's position in three dimensions by using a radar system to locate the distal end of the catheter. In one embodiment, the radar data can be combined with X-ray imagery to produce a composite display that includes radar and X-ray data. In one embodiment, the radar system includes a Synthetic Aperture Radar (SAR). In one embodiment, the radar system includes an ultra wideband radar. In one embodiment, the radar system comprises an impulse radar.

In one embodiment, the apparatus includes a user input device called a "Virtual Tip" that, in addition to being a representation of the actual or physical catheter tip advancing within the patient's body, possesses a positional relationship to the catheter tip. The Virtual Tip includes a physical assembly, similar to a joystick, that can be manipulated by the surgeon/operator and is also designed to deliver tactile feedback to the surgeon in the appropriate axis or axes if the actual tip encounters an obstacle. In other words, the Virtual Tip includes a joystick-type device that allows the surgeon to guide the actual catheter tip though the patient's body. When the actual catheter tip encounters an obstacle, the Virtual Tip provides tactile force feedback to the surgeon to indicate the presence of the obstacle.

In one embodiment, the physical catheter tip (the distal end of the catheter) includes a permanent magnet that responds to a magnetic field generated externally to the patient's body. The external magnetic field pulls, pushes, turns, and holds the tip in the desired position. One of ordinary skill in the art will recognize that the permanent magnet can be replaced or augmented by an electromagnet.

In one embodiment, the physical catheter tip (the distal end of the catheter) includes a permanent magnet and two piezoelectric rings, or semiconductor polymer rings to allow the radar system to detect the second harmonics of the resonating signal emanating from the rings.

In one embodiment, the GCI apparatus uses a technique of image synchronization by employing a sensor having six degrees of freedom (6-DOF), thereby enabling the formation of a stereotactic frame of reference.

In one embodiment, the electromagnetic circuit of the GCI apparatus includes a C-arm geometry using a ferromagnetic substance (e.g., a ferrite substance) so as to increase the efficiency of the magnetic circuit.

In one embodiment, the GCI apparatus uses numerical transformations to compute currents to be provided to various electromagnets to control the magnetic field used to push, pull and rotate the catheter tip in an efficient manner.

In one embodiment, the GCI apparatus includes an UWB impulse radar and a 6-DOF sensor configured to detecting the catheter tip and moving body organs, and synchronize their motions.

In one embodiment, the GCI apparatus is gimbaled by a motorized mechanism to allow the electromagnet poles of to be moved to a position and orientation that reduces the power requirements necessary to push, pull and rotate the catheter tip.

In one embodiment, the GCI apparatus is used to perform an implantation of a pace-maker during an electrophysiological (EP) procedure.

In one embodiment, the GCI apparatus uses radar or other sensors to measure, report and identify the location of a moving organ within the body (e.g., the heart, lungs, etc), with respect to the catheter tip and one or more fiduciary markers, so as to provide guidance control and imaging to compensate for movement of the organ, thereby simplifying the surgeon's task of manipulating the catheter through the body.

In one embodiment, the operator control provides the position and orientation command inputs to a servo system that controls the catheter tip position by regulating the magnetic force applied outside the patient's body. A measurement of the actual tip position and orientation is made via sensory apparatus that includes a radar system, and the 6-DOF sensor. This measurement is used to provide feedback to the servo system and the operator interface. In one embodiment, the servo system has a correction input that compensates for the dynamic position of a body part, or organ, such as the heart, thereby offsetting the response such that the actual tip moves substantially in unison with the beating heart.

In one embodiment, operation of the catheter guidance system is as follows: i) the operator adjusts the physical position of the virtual tip, ii) a change in the virtual tip position is encoded and provided along with data from a radar system and a 6-DOF sensor to a control system, iii) the control system generates servo-system commands that are sent to a servo system control apparatus, iv) the servo system control apparatus operates the servo mechanisms to adjust the position of one or more electromagnet clusters by varying the distance and the angle of the electromagnet clusters and energizing the electromagnets to cause the position of the actual magnetic catheter tip within the patient's body to change, v) the new position of the actual catheter tip is then sensed by the radar system and the position of a plurality of fiduciary markers are sensed by the 6-DOF sensor, thereby allowing synchronization and superimposing of the catheter position on an image produced by fluoroscopy and/or other imaging modality, and vi) providing feedback to the servo system control apparatus and to operator interface and updating the displayed image of the actual catheter tip position in relation to the patient's internal body structures.

The operator can make further adjustments to the virtual catheter tip position and the sequence of steps ii through vi are repeated. In one embodiment, feedback from the servo system control apparatus creates command logic when the actual catheter tip encounters an obstacle or resistance in its path. The command logic is used to control stepper motors which are physically coupled to the virtual catheter tip. The stepper motors are engaged as to create resistance in the appropriate directions that can be felt by the operator, and tactile feedback is thus provided to the user.

BRIEF DESCRIPTION OF THE DRAWINGS

The various features of the present are described with reference to the following figures.

FIG. 2B and FIG. 2M, are a representation of the geometrical layout of the coils, the arm and the table, the radar and the 6-DOF sensor.

FIG. 2D is a matrix representation of the vector forming the GCI system.

FIG. 2E is a representation of a characteristic matrix in the GCI system.

FIG. 2F is a representation of the Inverse characteristic matrix shown in FIG. 2E above.

FIG. 2G is a representation of the product of the characteristic matrix with its Inverse matrix used in the GCI system.

FIG. 2I is a front view showing the magnet clusters, radar system, and optical sensor.

FIG. 2J is a side view showing the magnet clusters, the radar system, the optical sensor, the C-arm, and an operating table.

FIG. 2K illustrates the radar system, the 6-DOF sensor, and a gimbaled motion mechanism on top of the C-arm.

FIGS. 6 and 6A are perspective views of a catheter assembly and a guidewire assembly for use in the CGCI apparatus.

FIG. 6B a representation of a catheter fitted with a magnetic tip and two piezoelectric rings.

DETAILED DESCRIPTION

In general, catheterization is performed by inserting an invasive device into an incision or a body orifice. Secondary tools such as guidewires and balloons are often advanced through or over the primary catheter to the area where the medical procedure is to be performed. These procedures rely on advancing the distal end of the invasive device until the distal end reaches the destination area where the diagnostic or therapeutic procedure is to be performed.

Figure 1:
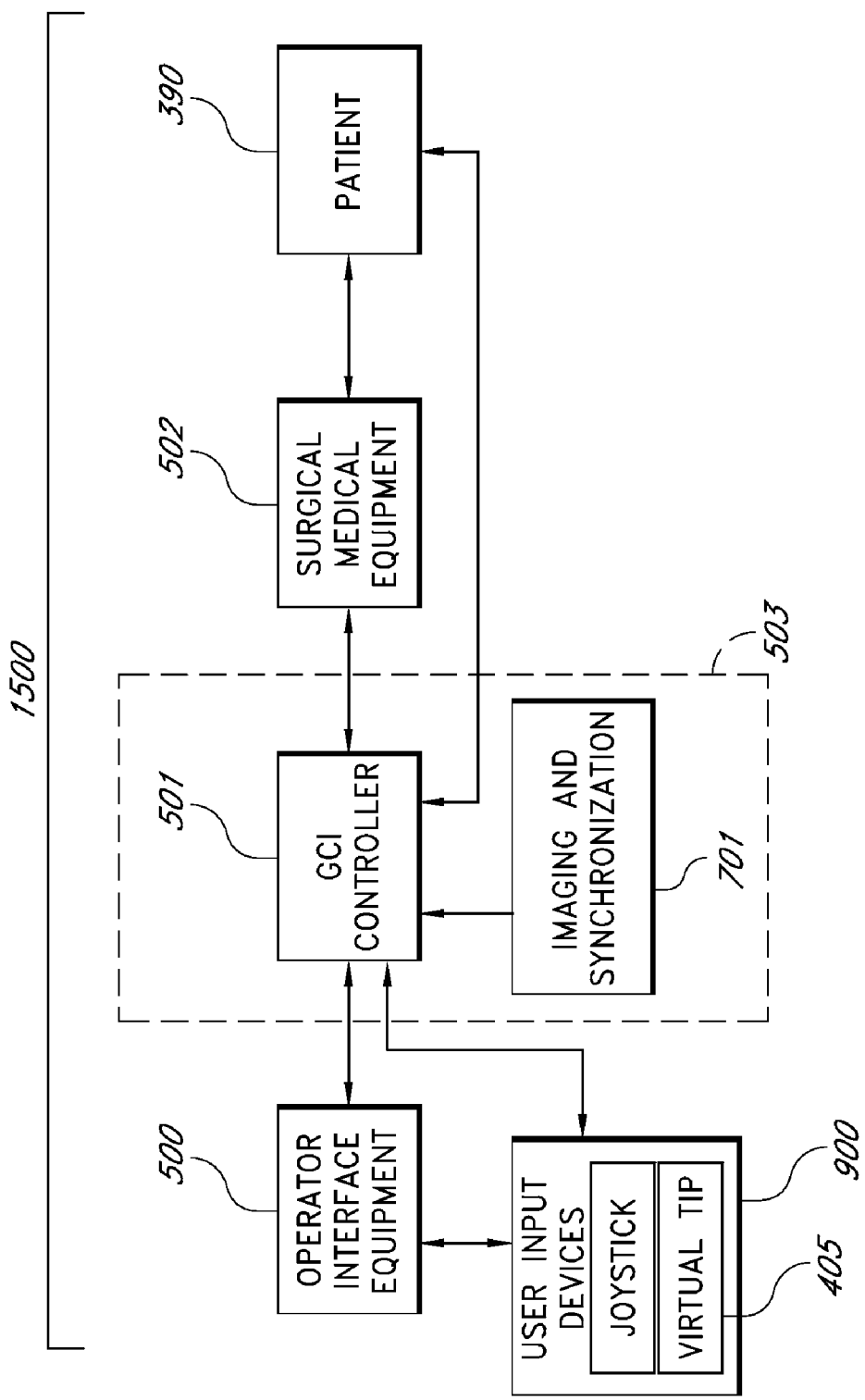
FIG. 1 is a high-level system block diagram for a surgery system that includes an operator interface, a catheter guidance system, surgical equipment (e.g., a catheter to be guided), an imaging and synchronization procedure, and a patient.

FIG. 1 is a system block diagram for a surgery system 1500 that includes an operator interface 500, a Catheter Guidance and Imaging (CGI) system 503, surgical equipment 502 (e.g, a catheter tip 377, etc.), one or more user input devices 900, and a patient 390. The user input devices 900 can include one or more of a joystick, a mouse, a keyboard, a Virtual Tip 405, and other devices to allow the surgeon to provide command inputs to control the motion and orientation of the catheter tip 377). The CGI system 503 includes a controller 501 and an imaging and synchronization module 701. The Figure illustrates the overall relationship between the various functional units and the operator interface 500, the auxiliary equipment 502, and the patient 390. In one embodiment, the GCI System Controller 501 calculates the Actual Tip (AT) position of a distal end of a catheter as further described in the text in connection with FIG. 7. Using data from the virtual tip (VT) 405 and the imaging and synchronization module 701, the GCI system controller 501 determines the position error, which is the difference between the actual tip position (AP) and the Desired tip Position (DP). In one embodiment, the controller 501 controls electromagnets to move the catheter tip in a direction selected to minimize the position error. In one embodiment, the GCI system 501 provides tactile feedback to the operator by providing force-feedback to the VT 405, as described in connection with FIG. 7 and FIG. 11.

Figure 1A:
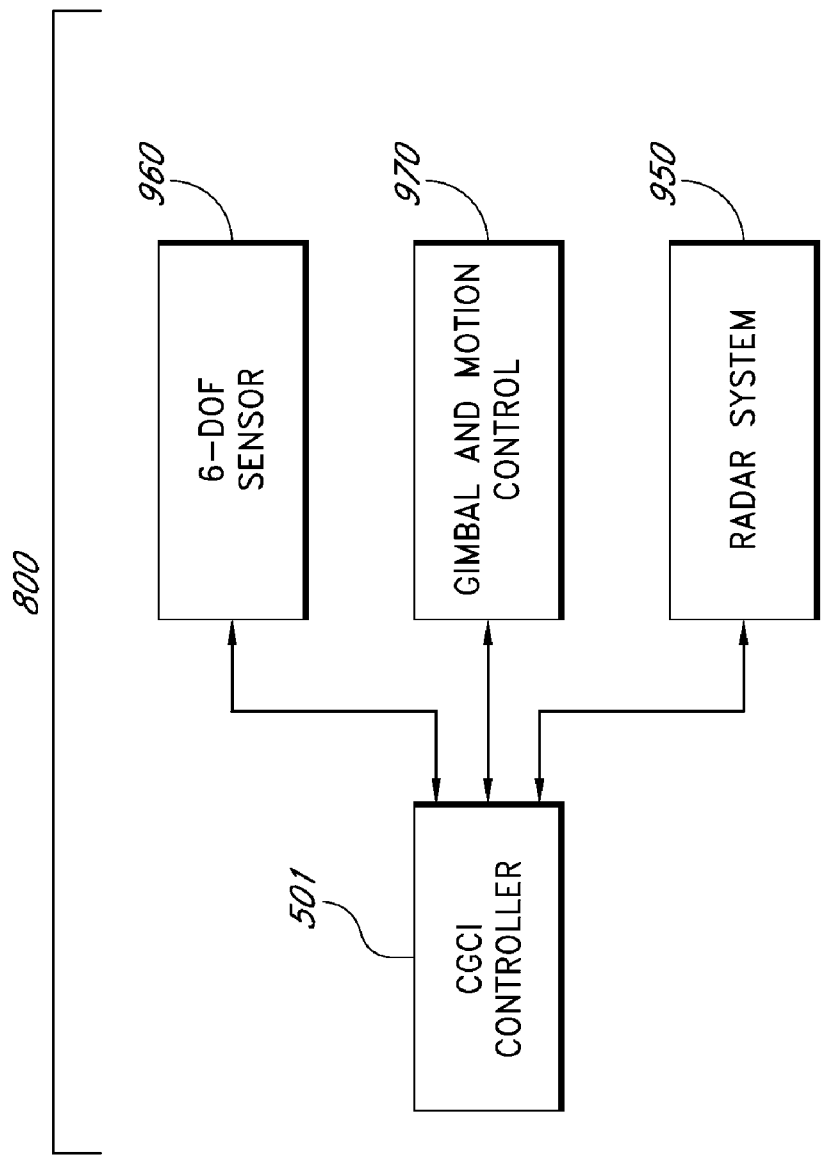
FIG. 1A is a block diagram of the imaging module for use in a GCI surgery procedure that includes the catheter guidance system, a radar system, a 6-DOF sensor, and a gimbaled motion mechanism.

FIG. 1A is a block diagram of a system for surgery system 800 that represents one embodiment of the GCI system 503. The system 800 includes the controller 501, a radar system 950, a position sensor 960, and (optionally) a gimbaled motion mechanism 970. In one embodiment, the sensor 960 includes a six Degrees-of-Freedom (6-DOF) sensor as described in connection with FIG. 10. The radar system 950 can be configured as a ultra-wideband radar, an impulse radar, a Continuous-Wave (CW) radar, a Frequency-Modulated CW (FM-CW) radar, a pulse-doppler radar, etc. In one embodiment, the radar system 950 includes a phase-array antenna. In one embodiment, the radar system 950 uses Synthetic Aperture Radar (SAR) processing to produce a radar image. In one embodiment, the radar system 950 includes an ultra-wideband radar such as described, for example, in U.S. Pat. No. 5,774,091, hereby incorporated by reference in its entirety. In one embodiment, the radar 950 is configured as a radar range finder to identifying the location of the catheter tip. The 6-DOF sensor 960 is configured to locate reference markers (fiduciary markers) placed on the patient. Data regarding location of the reference markers can be used, for example, for image capture synchronization. The motorized gimbaled and motion control mechanism 970 allows the electromagnets of the to be moved relative to the patient 390, as described in connection with FIG. 2K.

The use of radar for identifying the position of the catheter tip advantages over the use of Fluoroscopy, Ultrasound, Hall Effect Sensors, Magnetostrictive sensors, or SQUID. Radar can provide accurate dynamic position definition, which provides for real-time, high resolution, high fidelity signal. Radar is compatibility with strong magnetic fields. Self-calibration of range measurement can be based on time-of-flight or Doppler processing. Radar further provides for measurement of catheter position while ignoring "Hard" surfaces such as rib cage, bone structure, etc, as these do not interfere with measurement or hamper the accuracy of the measurement. In addition, movement and displacement of organ (pulmonary expansion and rib cage displacements as well as cardio output during diastole or systole) do not require an adjustment or correction of the radar signal. Radar can be used in the presence of movement since radar burst emission above 1 GHz can be used with sampling rates of 50 Hz or more, while heart movement and catheter dynamics occur at 0.1 Hz to 2 Hz.

The use of radar reduces the need for complex image capture techniques normally associated with expensive modalities such as fluoroscopy, ultrasound, Hall Effect Sensors, magnetostrictive technology, or SQUID which require computational-intensive processing in order to translate the pictorial view and reduce it to a coordinate data set. Position data synchronization of the catheter tip and the organ in motion is readily available through the use of the radar. Further, the radar can be used with a phased-array or Synthetic Aperture processing do develop detailed images of the catheter locating in the body and the structures of the body. In one embodiment, the radar system includes an Ultra Wide Band (UWB) radar with signal with a high resolution sweep range gate. In one embodiment, a differential sampling receiver is used to effectively eliminate ringing and other aberrations induced in the receiver by the near proximity of the transmit antenna. As with X-ray systems, the radar system can detect the presence of obstacles of objects located behind barriers such as bone structures. The presence of different substances with different dielectric constants such as fat tissue, muscle tissue, water, etc, can be detected and discerned due to attenuation variation. The outputs from the radar can be correlated with similar units such as multiple catheters used in Electro-Physiology (EP) studies while detecting spatial location of other catheters present in the heart lumen. The radar system can use a phased array antenna and/or SAR to produce 3-D synthetic radar images of the body structures, catheter tip, and organs.

The location of the patient relative to the CGI system (including the radar system 950) can be determined by using the 6-DOF sensor 960 to locate a plurality of fiduciary markers. Moreover, in one embodiment, the data from the sensor 960 is used to locate the body with respect to an imaging system such that the catheter position data from the radar can be superimposed (synchronized) with the images produced by the imaging system. The ability of the radar and the 6-DOF sensor to accurately position the catheter tip relative to the stereotactic frame, allows the CGCI electromagnet cluster to be moved by a gimbal system 970 so as to optimize the location of the magnet poles with respect to the patient and thus reduce the power needed to manipulate the catheter tip.

Figure 2A:
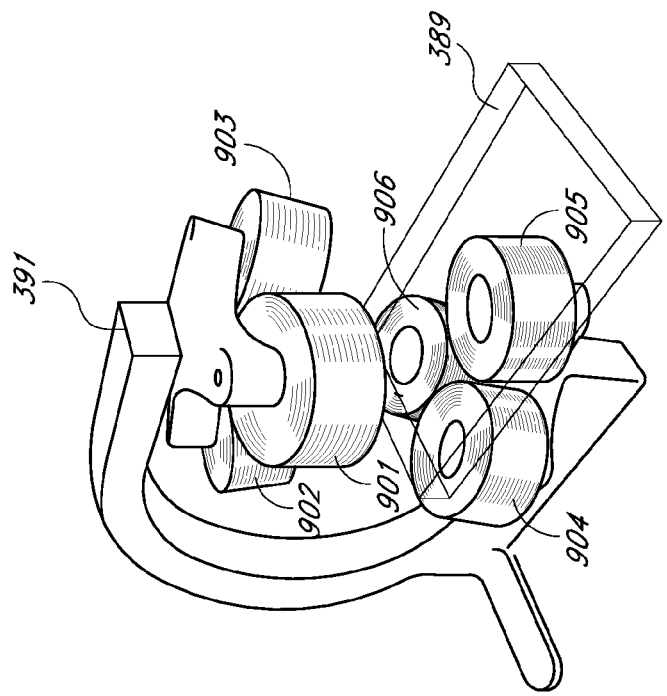
FIG. 2A shows a polar configuration in a cluster-like arrangement of electromagnets forming a magnetic circuit with a C-Arm.
Figure 2:
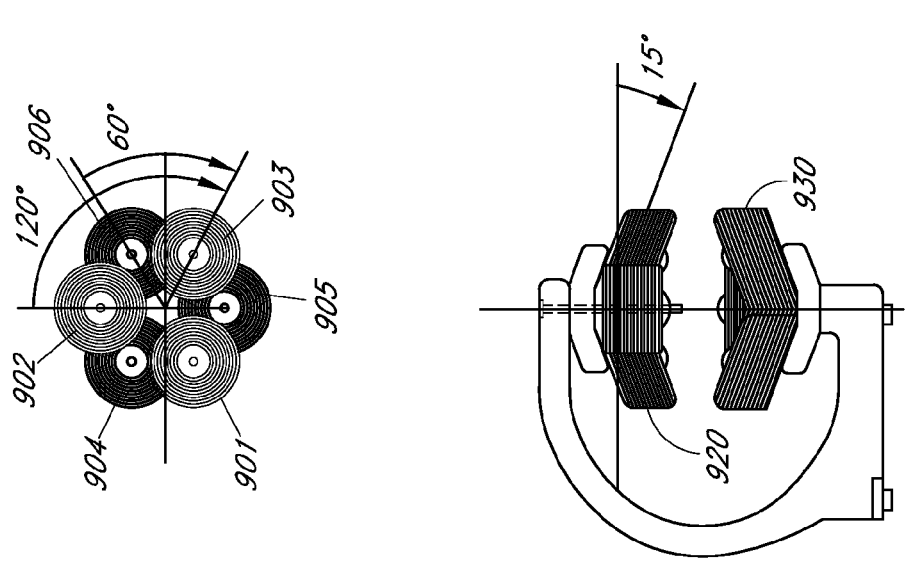
FIG. 2 is an orthographic representation view illustrating a polar configuration of the electromagnets.

FIGS. 2, 2A, and 2B show a polar configuration of electromagnets used in the GCI apparatus 503, with six coils 901-906 configured in flower-like structures, or clusters. The coils 901-903 are configured as a cluster 920 mounted at the top of a C-arm 391, and the coils 904-906 are configured as a cluster 930 mounted at the bottom of the C-arm 391. The three coils 901, 902 and 903, forming the upper cluster 920, are further shifted by 120 degrees relative to each other, as are the bottom three coils, 904, 905 and 906. In addition, the coils of cluster 920 at the top of the C-arm 391 are also tilted downward somewhat, at an angle of 15 to 20 degrees, as are the coils of the bottom cluster 930, of the C-arm 391, tilted upward, as shown in FIG. 2B. The C-arm 391 support assembly is configured to close the magnetic field circuit between the cluster 920 and the cluster 930. The cluster 920 at the top of the C-arm is rotated with respect to the bottom cluster by an angle of 60 degrees. An operating table 389 is provided between the cluster 920 and the cluster 930.

In FIG. 2B and FIG. 2M, the coils at the top of the C-arm 391 are marked as 901, 902, and 903, counting clockwise, and the bottom coils are marked 904, 905 and 906, counting in a counter clockwise direction. Coils 901 and 903 work as a pair and are designated as the X-axis pair of coils, coils 902 and 904 work as another pair and are designated as the Y-axis pair of coils, and coils 905 and 906 are the third pair and are designated as the Z-axis pair of coils (in this arrangement, the X, Y and Z coil axes are not orthogonal).

Figure 9:
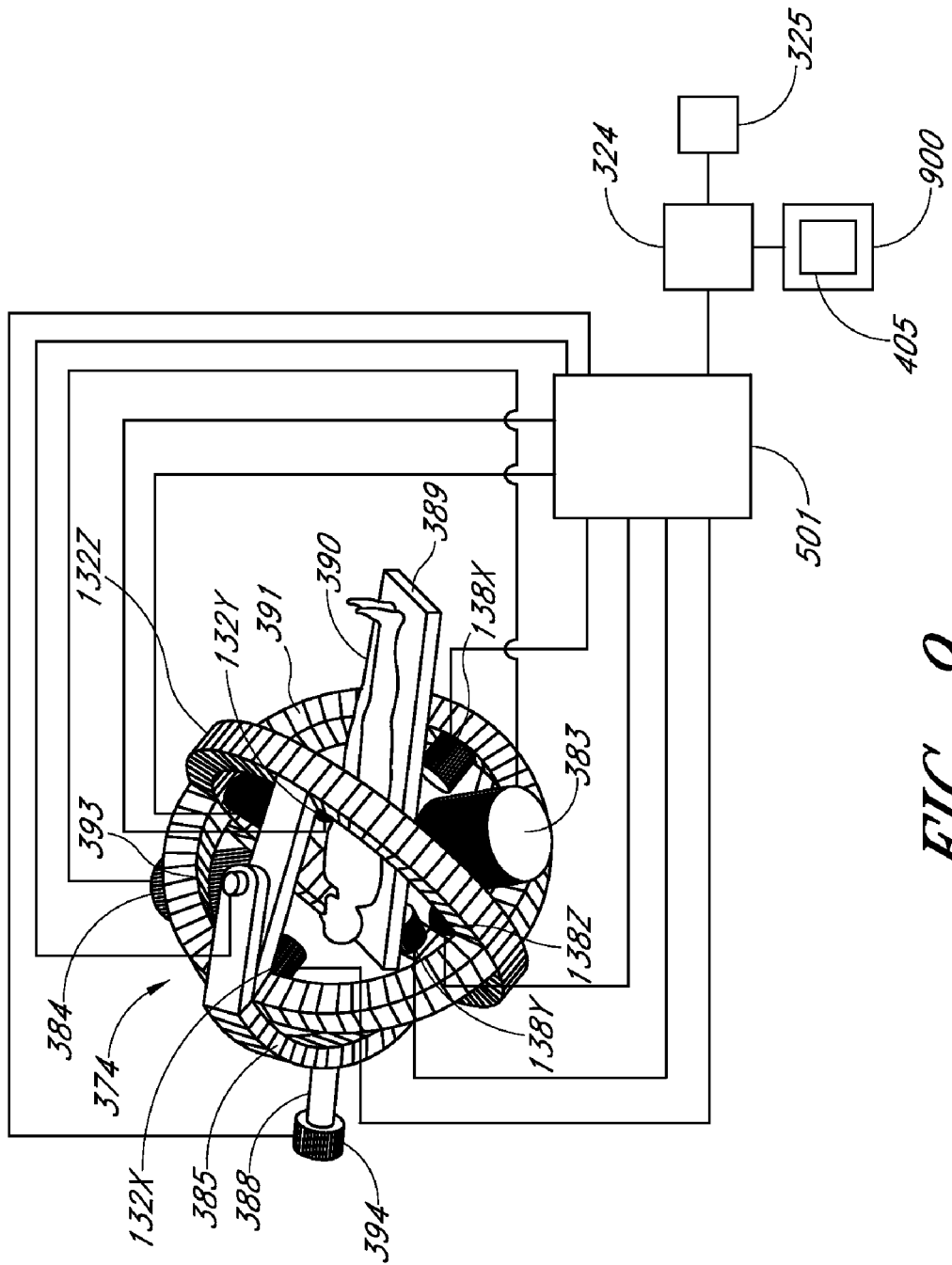
FIG. 9 shows use of the catheter guidance system combination with a stereoscopic image produce by a bi-plane dual X-ray system.

The cluster arrangement shown in FIGS. 2, 2A, and 2B provides for relatively free access for the physician to the patient while the Z axis electromagnets 905 and 906 do not obstruct the available access space. FIG. 9 shows an alternative embodiment using bi-plane rings. The embodiments of FIG. 2 and FIG. 9 are useful for accommodating imaging technologies such as X-ray, CAT-Scan, PET-Scan, Ultrasound, etc. The configuration shown in FIG. 9 allows the use of a stereoscopic image through the use of a bi-plane set-up with dual X-ray sources. FIGS. 2, 2A and 2B provide a geometry that is compatible with computer tomography systems and/or the imaging systems. The configurations shown in FIG. 9 and FIGS. 2, 2A and 2B provide for advantages in mounting the operating interface equipment 500, surgical medical equipment 502, and portions of the GCI apparatus 501.

Figure 2C:
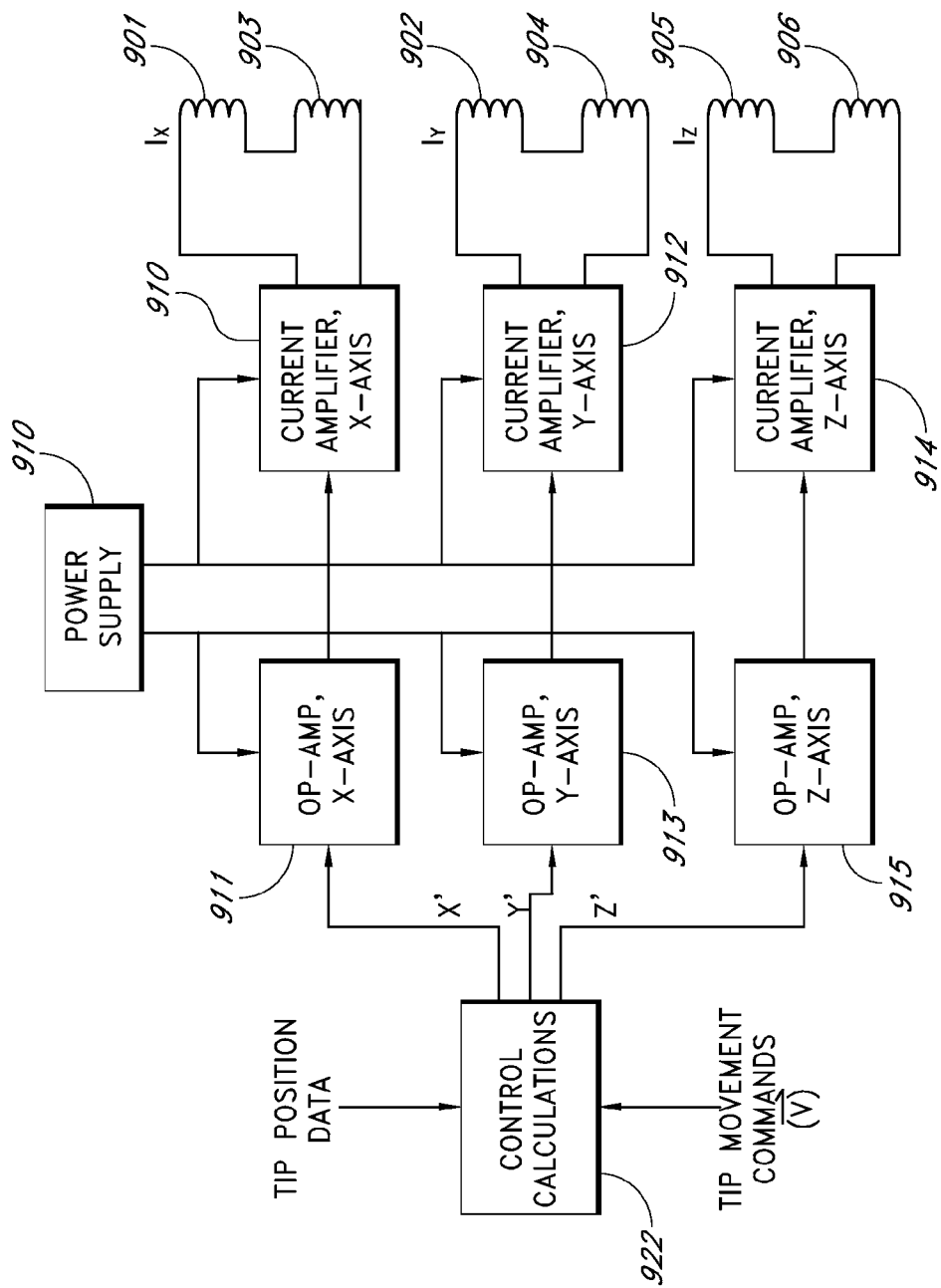
FIG. 2C is a block diagram of a system for driving electromagnet coils.

FIG. 2C is a block diagram of the drive system for the coils 901-906. The controller 530 calculates a desired X-axis drive signal that is provided to an X-axis op-amp 911. An output of the X-axis op-amp is provided to a current amplifier 910. The current amplifier 910 provides current to drive coils 901 and 903 in series. Alternatively, the coils 901, 903 can be driven in parallel (not shown). The controller 530 calculates a desired Y-axis drive signal that is provided to a Y-axis op-amp 913. An output of the Y-axis op-amp is provided to a current amplifier 912. The current amplifier 912 provides current to drive coils 902 and 904 in series. Alternatively, the coils 902, 904 can be driven in parallel (not shown). The controller 530 calculates a desired Z-axis drive signal that is provided to a Z-axis op-amp 915. An output of the Z-axis op-amp is provided to a current amplifier 914. The current amplifier 914 provides current to drive coils 905 and 906 in series. Alternatively, the coils 905, 906 can be driven in parallel (not shown). A power supply 899 provides power to the amplifiers 910-915.

Figure 2H:
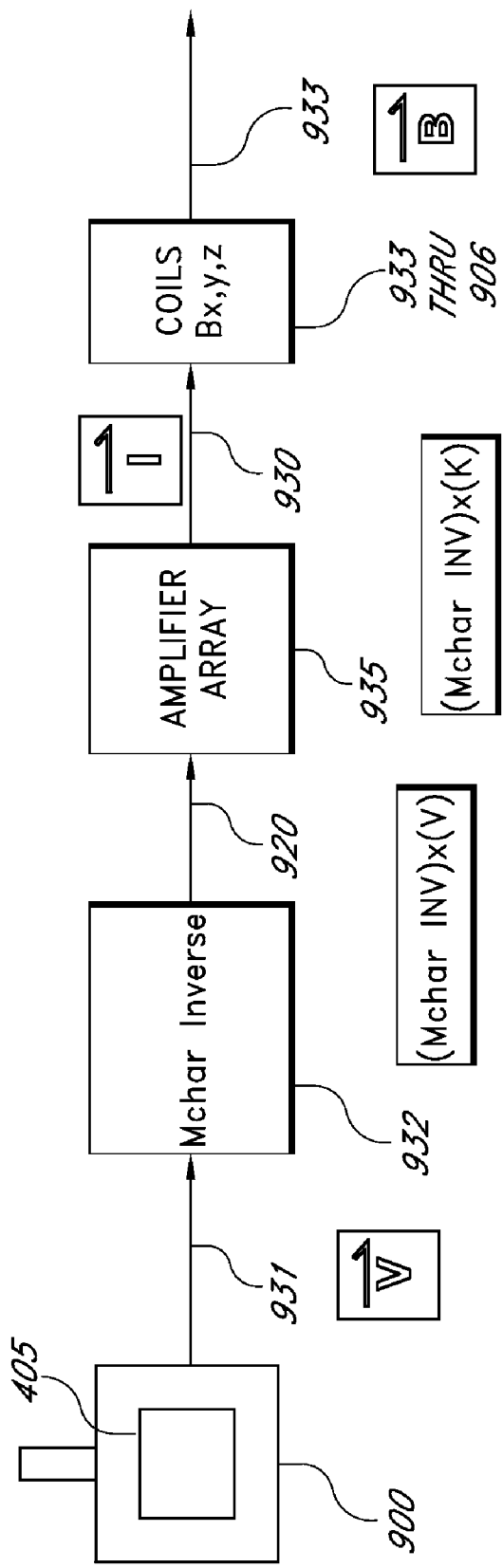
FIG. 2H is a logical flow diagram of FIG. 2G.

The signals for the three channels, X, Y, and Z, can be expressed as a vector V 923 shown in FIG. 2D, having elements $Vj_x$, $Vj_y$, and $Vj_z$. The operator uses the user input devices 900 such as the virtual tip 405 to command a movement in one or more axes. Signals from the user input devices 900 are provide to a computation module 922. In a closed-loop system, tip position data from a sensor such as the radar sensor 950 is also provided to the computation module 922. In an open-loop system, the tip position data is not necessarily provided. The computation module 922 translates the position data and perform an Inverse operation on the matrix of the three signals for the three axes. The computation module 922 multiplies the position vector V 923 by a matrix M-inverse, shown in FIGS. 2F and 2G as 927, such that the output of the computation module 922 is M-inverse times V, where M is the characteristic matrix 925 of the cluster of coils 901 through 906. The transformed X, Y, Z outputs from the computation module 922 are provided to the respective amplifiers 911, 913, and 915 to generate the magnetic field and thereby move the catheter dip in the direction commanded by the operator. The transformation of inputs in an open-loop system is shown in block diagram form in FIG. 2H, where the input signal V 931 is provided to an Mchar-Inverse module 932. The module 932 computes the matrix product Mchar-Inverse and the vector V to produce a transformed coordinate vector. The transformed coordinate vector is provided to amplifier array 935, that produces output currents that are provided to the respective current to the coils 901-906. The coils 901-906 produce the resulting field vector B 933. The field vector B 933 causes movement of the catheter tip, thereby translating the hand-movement of the clinician into the appropriate signal, and thus moving the catheter tip to the desired location.

FIG. 2K shows the radar system 950, the 6-DOF sensor 960, and a gimbaled motion mechanism 970 in relation to the C-arm 391, the clusters 920, 930 and the operating table 389. The motion mechanism 970 is configured to move the magnet cluster 920 to orient the cluster 920 in order to optimize (e.g, reduce) the power requirements for the operation of the electromagnets 901-906. The mechanical arrangement shown in FIG. 2K allows the GCI system 503 to be motion-controlled and gimbaled using motorized machinery 970 such as, for example, Computer Numeric Control (CNC) equipment. Use of the motorized gimbaled and computer-controlled mechanism 970 substantially reduces the overall power requirement for the system, thereby enabling a desired magnetic field-strength to be achieved with less power. In one embodiment, the desired magnetic field strength is at least 0.3 Tesla.

Figure 2L:
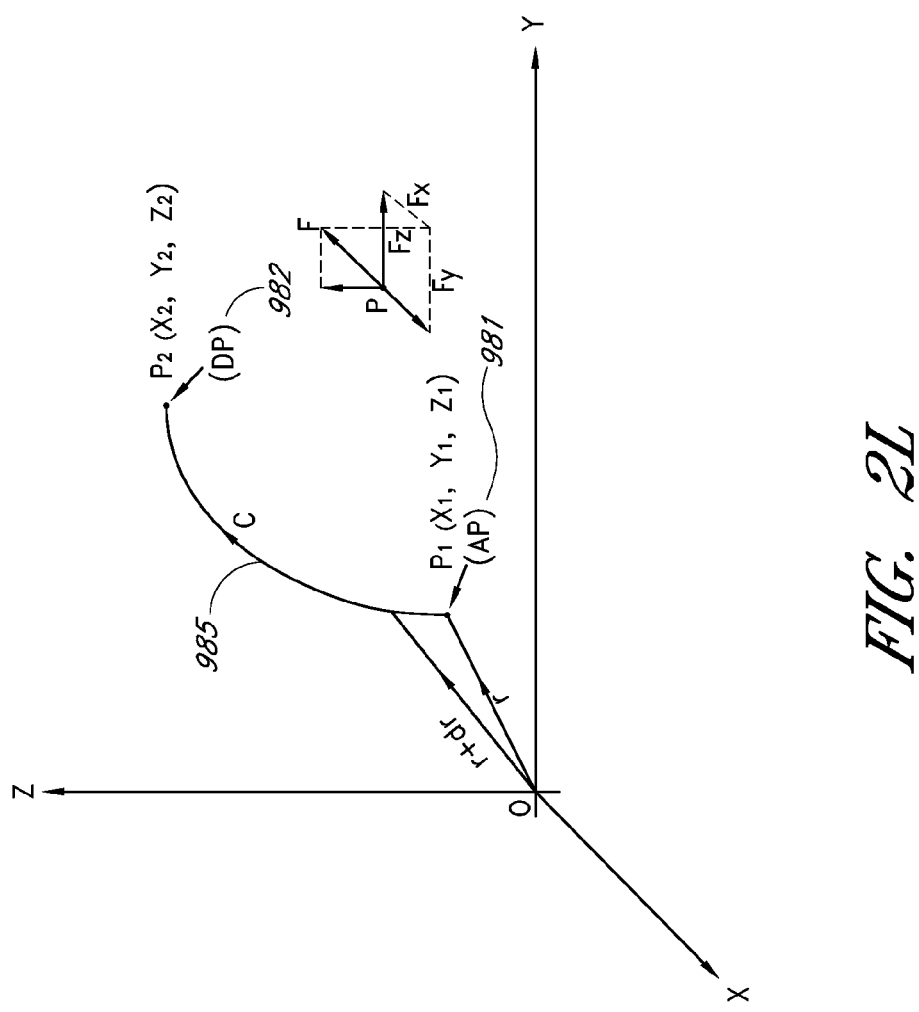
FIG. 2L illustrates a "C" curve representation of Actual Position (AP) of the catheter tip and the Desired Position (DP).

FIGS. 2K and 2L illustrate the use of the motorized, gimbaled, and computer-controlled mechanism 970 to adjust the distance r 971 of the upper electromagnet cluster 920 relative to the lower electromagnet cluster 930, so as to achieve an optimal power setting for the coils while maintaining a desired magnetic field strength. This procedure is achieved by first finding the location of the catheter tip 377 relative to the electromagnets by the use of the radar system 950 and synchronizing the position of the catheter tip 377 with fiduciary markers 700Ax through 700Bx (also referred to as reference markers 700Ax through 700Bx) by the use of the 6-DOF sensor 960. The reference markers 700Ax through 700Bx are placed on the patient to provide reference points. This arrangement generates a mathematical manifold 701 (as described in connection with FIG. 7) over an image 702 generated by a fluoroscopic or other imaging system. The distance between the actual position (AP) 981, of the catheter tip 377 is marked by P1 and the desired position (DP) 982, set by the surgeon and is marked by P2. The difference between the two co-ordinates P1 and P2 is a position error (PE) 983. The force F and the resultant electromagnetic field B are then calculated by the GCI controller 501 as described in connection with FIGS. 2C-2H. This process finds the position error (PE) 983, which the controller 501 translates into the necessary current I for the coils 901-906. The controller then changes the distance r 971, and the angle Φ 984, of the upper electromagnet cluster 920 relative to the lower electromagnet cluster 930 while the mechanism 970 is gimbaled and controlled, so as to set the distance r and the angle Φ 984 of the electromagnet clusters 920 relative to 930 in order to achieve an optimal power setting for the performance of GCI apparatus 503. Once the position of the cluster 920 relative to cluster 930 is set by the controller, the controller feeds the electromagnets with the calculated current I to produce the desired movement of the catheter tip 377. This procedure of adjusting the distance r 971, and the angle Φ 984, of the electromagnet clusters 920 relative to 930 so as to achieve the optimal power setting for GCI apparatus 501 can be described by the line integral designated by equation (1) below, where a point P is calculated in space (P is the position co-ordinates of the catheter tip 377 in the patient 390) by integrating the function with respect to the vector $r=i_x, j_y+k_z$ which denotes the position of the catheter tip 377 at any point P (x,y,z) on the "C" curve 985. The "C" Curve 985 is the line integral formed between point P1 (the actual position (AP) 981 of the catheter tip 377) and point P2 (the desired position 982 set by the operator/surgeon). The "C" curve 985 is then integrated with respect to the distance to calculate the force F necessary to move the catheter tip 377 from P1 to P2. The line integral adjoining the two points in question, the actual position of the tip (AP) and the desired position (DP), is:

$$\int_{P_1}^{P_2} F \cdot dr = \int_{x_1}^{x_2} F_x dx + \int_{y_1}^{y_2} F_y dy + \int_{z_1}^{z_2} F_z dz \quad (1)$$

The force F and the resultant electromagnetic field B correspond to the appropriate current requirement I so as to achieve an optimal power setting in order to push, pull and rotate the catheter tip 377 thereby bringing it to its desired location. Thus the only variable is the current vector I as the gimbal varies the value of the distance r 971.

Figure 3:
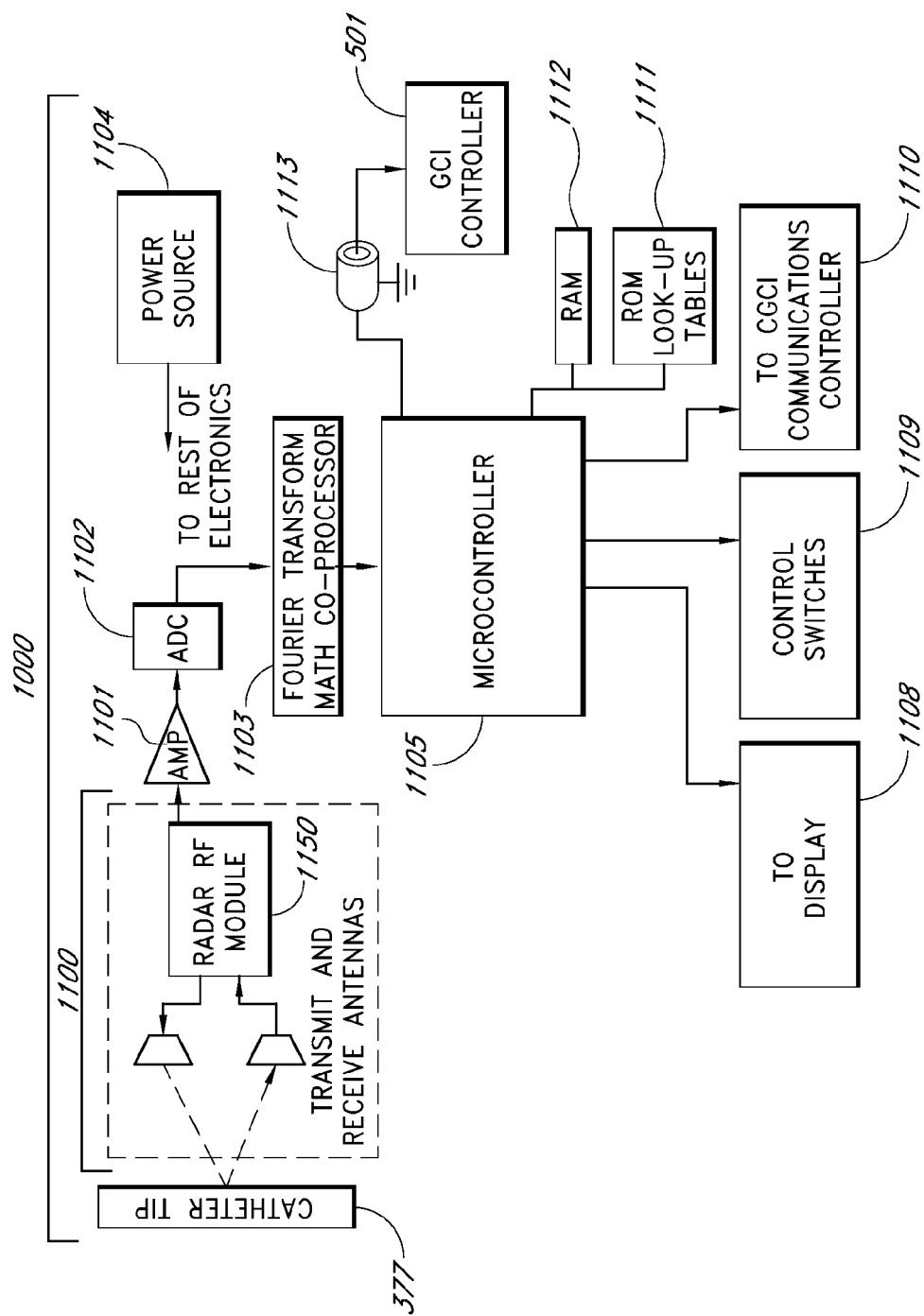
FIG. 3 is a block diagram of the radar Phased-array Radar module and its associated electronics for measuring the position of the catheter.

FIG. 3 is a block diagram of a radar system 1000 that can be used as one embodiment of the radar system 950. The radar 1000 shown in FIG. 3 includes a phased-array radar module 1100 having transmit/receive antenna elements and a Radio Frequency (RF) module 1150. The radar system 1000 includes the phased-array 1100, an amplifier 1101, an A/D converter 1102, a Fast Fourier Transform module 1103, and a microcontroller 1105. The apparatus further includes a memory module in the form of RAM 1112, and a look-up table in the form of a ROM 1111. One embodiment includes a voice messaging and alarm module 1110, a set of control switches 1109, and a display 1108. The data generated by the radar system 1000 is provided to the GCI apparatus 501 via communications port 1113.

The radar system 1000 includes a phased-array and uses Microwave Imaging via Space-Time (MIST) beam-forming for detecting the catheter tip 377. An antenna, or an array of antennas, is brought relatively near the body of the patient and an ultra wideband (UWB) signal is transmitted sequentially from each antenna. The reflected backscattered signals that are received as radar echoes are passed through a space-time beam-former of the radar unit which is designed to image the energy of the backscattered signal as a function of location. The beam-former focuses spatially the backscattered signals so as to discriminate it from the background clutter and noise while compensating for frequency-dependent propagation effects. The significant contrast between the dielectric properties of normal tissue and the catheter tip 377 (formed out of a ferrite such as samarium-cobalt SmCo5, or neodymium-iron-boron, NdFeB, etc.), in the regions of interest, sufficient backscatter energy levels in the image to distinguish normal tissue from the catheter tip 377, affording detection and discernability. A data-adaptive algorithm is used in removing artifacts in the received signal due to backscatter from the body tissue interface (e.g. the skin layer). One or more look-up tables containing the known dielectric constants of the catheter tip contrasted against the background dielectric information relative to the biological tissue can be used to identify features in the radar image.

The physical basis for microwave detection of the catheter tip 377 in the biological tissue is based on the contrast in the dielectric properties of body tissue versus the signature of the catheter tip 377. The contrast of the dielectric values of biological tissue versus that of the catheter tip is amplified, filtered and measured. As a result, the catheter tip 377 has a microwave scattering cross-section that is different relative to biological tissue of comparable size, relative to their dielectric properties, which is indicated by greatly different backscatter energy registered by the receiver, and processed so as to afford a pictorial representation on a monitor 325 (shown in FIG. 5), with a significant contrast between the two mediums. The pictorial view of the catheter tip 377 generated by the radar system 1000 can be superimposed over an X-ray fluoroscopy image and its coordinate data set linked to the GCI controller 501 for use by the position servo feedback loop. Hence microwave imaging via space-time (MIST) beam-forming is used for detecting backscattered energy from the catheter tip 377 while the background is biological tissue.

The radar system 1000 detects the presence and location of various microwave scatterers, such as the catheter tip 377, embedded in biological tissue. The space-time beam-former assumes that each antenna in an array transmits a low-power ultra-wideband (UWB) signal into the biological tissue. The UWB signal can be generated physically as a time-domain impulse or synthetically by using a swept frequency input. In one embodiment, the radar system 1000 uses a beam-former that focuses the backscattered signals of the catheter tip 377 so as to discriminate against clutter caused by the heterogeneity of normal tissue and noise while compensating for frequency-dependent propagation effects. The space-time beam-former achieves this spatial focus by first time-shifting the received signals to align the returns from the targeted location. One embodiment of the phased-array radar 1000 forms a band of finite-impulse response (FIR) filters such as high dielectric doping in the antenna cavity, forming the reference signal, where the doping is relative to the device of interest. The signals from the antenna channels are summed to produce the beam-former output. A technique such as weights in the FIR filters can be used with a "least-squares fitting" technique, such as Savitzky-Golay Smoothing Filter, to provide enhancement of the received signal and to compute its energy as a function of the dielectric properties versus the scattered background noise of body tissue, thereby providing a synthetic representation of such a signal. The system can distinguish differences in energy reflected by biological tissues and the catheter tip 377 and display such energy differences as a function of location and co-ordinates relative to the fiduciary markers 700Ax through 700Bx, thereby providing an image proportional to backscattered signal strength, which is further used by the GCI controller 501 in computing the position co-ordinates and orientation of the catheter tip 377 relative to the stereotactic framing of the fiduciary markers. The details of the formation of the co-ordinates settings of the catheter tip 377 relative to the stereotactic frame and the synchronization of such image with the fluoroscopy frame 702 is further described in connection with FIGS. 5 and 5A. In one embodiment, the radar module 1000 uses an FFT algorithm 1103 which uses a filtering technique residing in look-up tables 1111 to allow the radar sensor 950 to discern varieties of dielectric properties of specific objects known to be used in a medical procedure, such as a guide-wire 379 and/or a catheter 953 with piezo-electric ring 951, 952, so as to afford differentiation of various types of instruments like catheters, guide-wires, electrodes, etc.

Figure 3B:
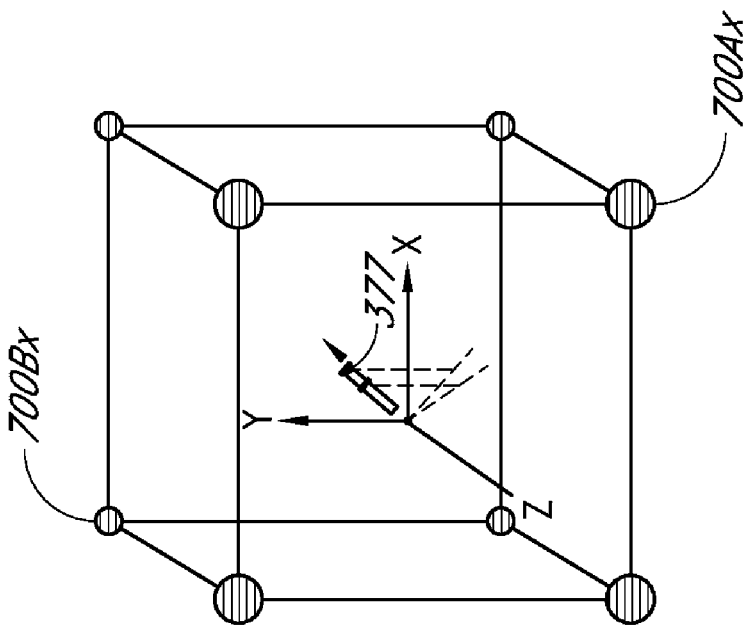
FIG. 3B illustrates locating the catheter in a field of fiduciary markers.
Figure 3A:
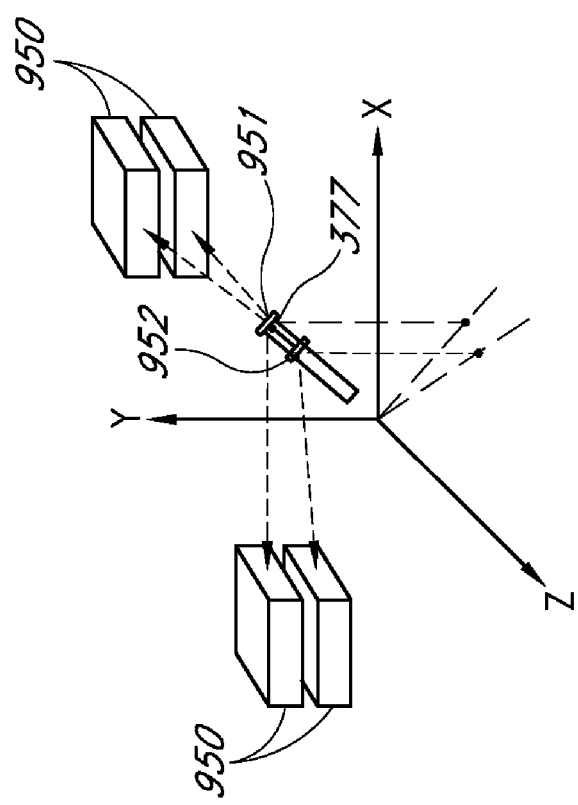
FIG. 3A illustrates the use of the radar system in identifying the position and orientation of the catheter tip.

FIG. 3A is a graphical representation of the catheter tip 377 embedded with one or two piezoelectric rings 951, 952 such as Lead-Zirconate-Titanate (PZT) and/or molecularly conjugated polymers such as switchable diodes (polyacetylene). The second harmonics generated by the rings 951, 952 provide an identifiable return signature in the second harmonic due to the non-linearity of the material. While the fundamental harmonic (e.g. 5 MHz) is transmitted by the radar, the second harmonic (e.g. 10 MHz) is readily distinguishable by the radar system 1000. The radar system 1000 can discern between the catheter tip (which is formed out of ferrite such as samarium-cobalt SmCo5, or neodymium-iron-boron, NdFeB) and the PZT rings 951 and 952. The ability to distinguish between the signal return from catheter tip 377 and the PZT rings 951, 952, allows the radar system 1000 to filter out the background clutter received from the body tissue and recognize the position and orientation of the rings 951, 952, and the position co-ordinates of the catheter tip 377. The technique of using two different dielectric properties and electrical characteristic of the tip 377 versus the PZT 951 and 952 provides the catheter tip 377 with a radar signature that is unique and readily recognized by the radar system 1000.

FIG. 3A further illustrates how the radar system 1000 with its transmit and receive antennas is used to detect the position co-ordinates and orientation of catheter tip 377 relative to its two PZT rings 951 and 952. A geometrical manipulation is employed by the radar system 1000 and its associated FFT filter 1103 by the resident microcontroller 1105. As shown in FIG. 6B, a catheter-like device is provided with a magnetically-responsive tip 377. In one embodiment, the tip 377 includes a permanent magnet. The polarity of the permanent magnet is marked by two PZT rings where the north pole is indicated by a PZT ring 952 and the distal end of the ferrite where the semi-flexible section 953 of the catheter 376 is marked with the additional PZT ring 951, also marking the south pole of the ferrite. The radar system 1000 transmits burst of energy that illuminates the ferrite catheter tip 377. The return signal from the catheter tip 377 is received by the radar and its position is registered by observing the time of flight of the energy, thereby determining the location of the catheter tip 377 as position co-ordinates in a three-dimensional space. By employing the two PZT rings 951 and 952, the radar detector 1000 is also capable of discerning the location of the tip 377 relative to the two PZT rings so as to afford a measurement of PZT ring 952 relative to the second piezo-electric ring 951 with reference to the position co-ordinates of catheter tip 377. The radar detector 1000 can discern the return signal from PZT rings 952 and 951 due to the non-linear characteristic of PZT material that generates a second harmonic relative to the incident wave. By comparing the strength of the fundamental frequency and the second harmonic, the radar system 1000 is able to discern the position and orientation of the two PZT rings relative to the ferrite 377, thereby providing position and orientation of the catheter tip 377.

Figure 4:
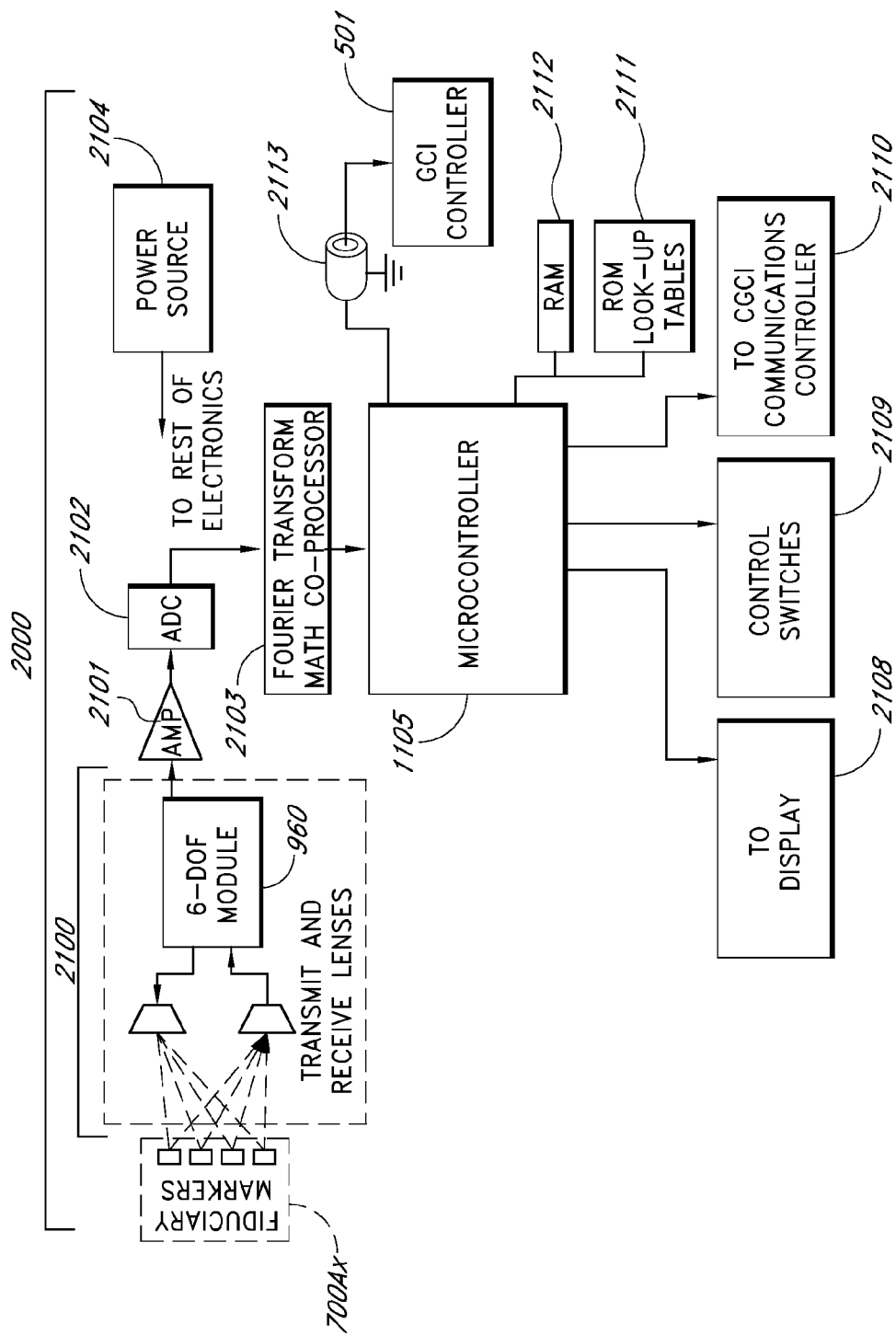
FIG. 4 is a block diagram of the 6-DOF sensor and its associated electronics for measuring the location of the fiduciary markers and synchronization of the image-capture.
Figures 5, 5A:
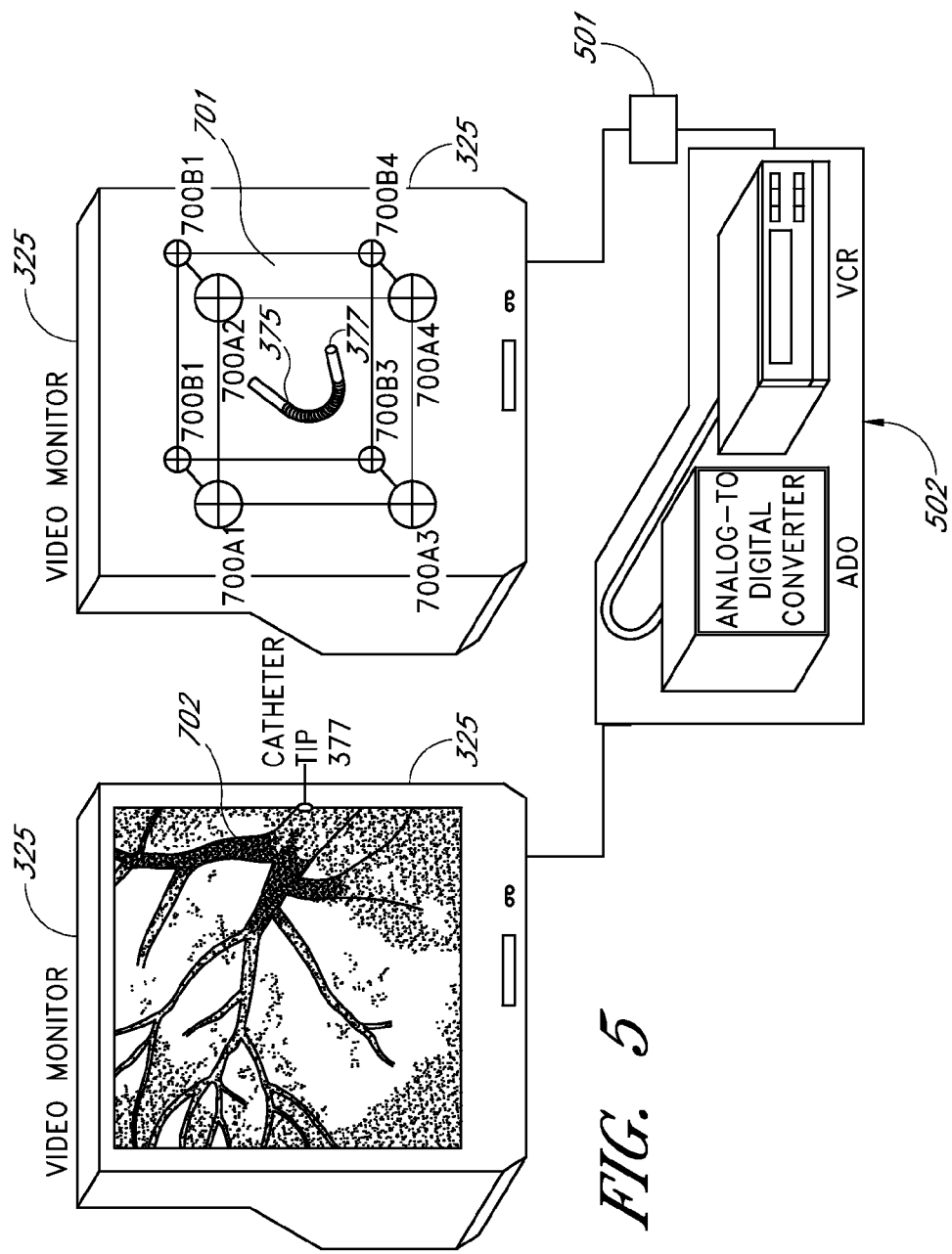
FIG. 5 illustrates the use of the GCI apparatus with cineoangiographic equipment.
FIG. 5A shows how a fluoroscopy image and the synthetic image of the catheter from radar data are synchronized using the fiduciary markers and the 6-DOF sensor.
Figure 5B:
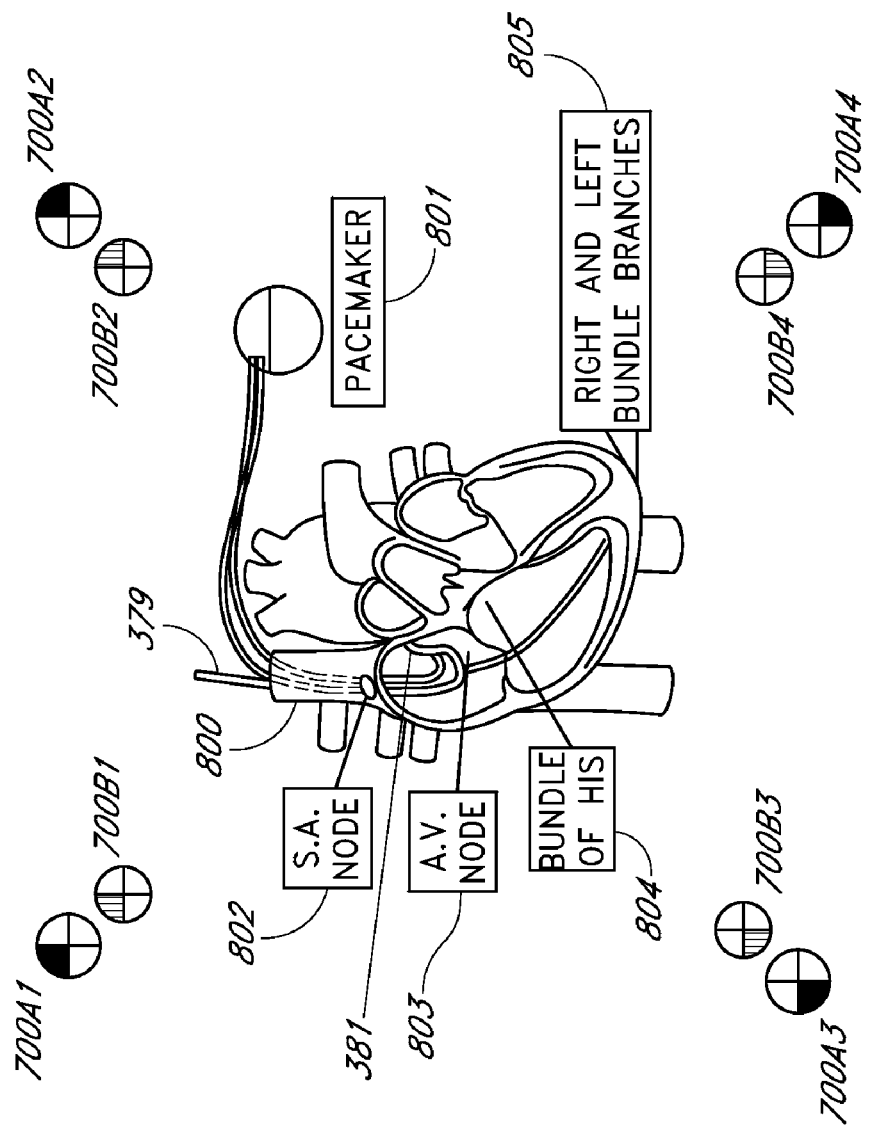
FIG. 5B illustrates the use of the apparatus noted in 5A while performing a pacemaker electrode implantation.

FIGS. 3B, 5 and 5B illustrate the technique of measuring the position and orientation of the catheter tip by the use of the radar detector 1000 and using the fiduciary markers 700Ax and 700Bx to form a frame of reference for the catheter dynamics such as movement relative to the frame of reference. As shown in FIGS. 3B and 5B the fiduciary markers 700Ax and 700Bx form a manifold 701. The locations of the markers 700Ax and 700Bx are measured by the 6-DOF sensor FIG. 4 is a block diagram of a 6-DOF sensor system 2100 that is one embodiment of the 6-DOF sensor 960. The system 2001 includes a 6-DOF optical sensor 2100 and its associated electronics for measuring the location of the fiduciary markers 700A1, 700A2, 700A3, and 700A4, and 700B1, 700B2, 700B3, and 700B4, located on the patient's body 390 to define a stereotactic frame. As shown in FIG. 5, the fiduciary markers 700A1, 700A2, 700A3, and 700A4, and 700B1, 700B2, 700B3, and 700B4 allow synchronization 701 of the image 702 shown on a video monitor 325, with the location of the catheter tip 377. The 6-DOF optical sensor 2100 is described in more detail in connection with FIG. 10. The system 2000 includes the 6-DOF optical sensor 2100, an instrumentation amplifier 2101, an A/D converter 2102, a Fast Fourier Transform module 2103, and a microcontroller 2105. One embodiment includes a voice massaging and alarm module 2110, a set of control switches 2109, and a display 2108. Data generated by the 6-DOF sensor 2000 is provided to the GCI apparatus 501 via a communications port 2113.

FIG. 5 illustrates a general connection of the GCI apparatus 501 to cineoangiographic equipment 502. The cineoangiographic equipment 502 is interfaced with the GCI apparatus 501 through the operator interface equipment 500. The cineoangiographic image of an arterial tree is shown on the video monitor 325, with the position of catheter tip 377 superimposed onto the image. For convenience in the present description, and not by way of limitation, the image will be referred to herein as a flouroscopy image, it being understood that the image can be generated by any technology that can generate images of the body structures, including, but not limited to, X-ray imaging, Fluoroscopy, ultrasonic imaging, MRI, CAT-Scan, PET-Scan, radar imaging, etc. The display of these images is synchronized by the use of the 6-DOF sensor and its accompanying fiduciary markers 700A1, 700A2, 700A3, and 700A4, and 700B1, 700B2, 700B3, and 700B4, located on the patient's body 390 so as to locate a stereotactic frame that provides for the referential markers and enables the synchronization 701 of the image 702 shown on video monitor 325, with the position of the catheter tip 377.

FIG. 5A illustrates how the image 702 and the synthetic image of the catheter 377 obtained from the radar system 950 are superimposed together on monitor 325 and synchronized using the 6-DOF sensor 2000 and the fiduciary markers 700A1, 700A2, 700A3, and 700A4, and 700B1, 700B2, 700B3, and 700B4, located on the patient's body 390. FIG. 5A further illustrates the formation of a stereotactic frame 701 in support of position definition of the catheter tip 377 relative to the frame 701. This method uses fiduciary markers formed as an approximate cube and detected by the 6-DOF sensor 2100. The entire data set formed as a manifold 701 includes a set of the image 702, radar image data of catheter tip 377 (such as, for example, data from the radar system 1000), and the fiduciary markers 700Ax through 700Bx.

Synchronization of the image of the catheter tip 377 or guide wire 379, captured by the radar system 950, is superimposed onto the fiduciary markers which are represented digitally and are linked dynamically with the image 702. This is done so as to create one combined manifold 701, which is superimposed onto the fluoroscopic image 702, and moves in unison with the area of interest relative to the anatomy in question. For example, the beating heart and its cardio-output, the pulmonary expansion and contraction, or a spasm of the patient, all these can be dynamically captured and linked together so as to achieve a substantial motion in unison between the catheter's tip and the body organ in question.

FIG. 5A further illustrates the image capture technique of superimposing the fiduciary markers 700A1, 700A2, 700A3, 700A4, 700B1, 700B2, 700B3, and 700B4 on the fluoroscopic/ultrasonic image 702, generated as shown in the image in FIG. 5. The scheme provided identifies the dynamic location of the catheter tip 377 with reference to the image 702. The referential frame 701 formed by the fiduciary markers 700Ax and 700Bx and utilizing the 6-DOF sensor 2000, defines the catheter's tip position relative to the stereotactic frame 701. Furthermore, by employing a technique of geometric projection, this method provides for a synchronized image-capture relative to the catheter tip 377 thereby affording the superimposition of the image 702 relative to both the fiduciary markers 700Ax and 700Bx and the catheter tip 377 on a dynamic basis, hence, providing position definition with a frame of reference, noted in FIG. 5A as 701.

FIG. 5A shows the use of the synchronization algorithm 701 whereby the space formed by the fiduciary markers 700A1, 700A2, 700A3, 700A4, 700B2, 700B3, and 700B4 is represented by an n-dimensional space where each of the fiduciary markers 700Ax and 700Bx is denoted by a vector $f_i$ $\{f_1, f_2 \ldots f_n\}$ and the catheter tip 377 position data provided by the radar 1000 are designated by a function $g_i$ $\{g_1, g_2 \ldots g_n\}$. The length of the vector f, g in an n-dimensional space is defined by $$(701) \sqrt{\sum_{i=1}^{n} f_i^2} .$$

The sum on the space is taken by the integral $$\sqrt{\int_a^b f^2(x) dx} ,$$

further the distance between the point f (fiduciary markers) and g (catheter tip 377 position) in an n-dimensional space is $$\sqrt{\sum_{i=1}^{n} (f_i - g_i)^2} ,$$

thus $$\sqrt{\int_a^b [f(t) - g(t)]^2 \, dt} \quad (2)$$

This result is the square deviation of the functions f(t) and g(t). The angle between the vectors definition of 700Ax, 700Bx, $f_i$ and vector definition of the catheter tip 377 $g_i$ is denoted by cos $$\Phi = \frac{\sum_{i=1}^{n} f_i g_i}{\sqrt{\sum_{i=1}^{n} f_i^2} \sqrt{\sum_{i=1}^{n} g_i^2}}$$

and in thus $$\cos\Phi = \frac{\int_a^b f(t) g(t) dt}{\sqrt{\int_a^b f^2(t) dt} \sqrt{\int_a^b g^2(t) dt}} \quad (3)$$

since $f_i$ and $g_i$ are orthogonal ($\int_a^b f(x)g(x)dx=0$).

The 6-DOF 2000 sensor with its position data set as a vector function $f_i$ and the position data set of the catheter tip 377 generated by the radar system 1000 and denoted by vector function $g_i$ are orthogonal and their distance is shown by the difference noted in equation (2) and its relative orientation is shown by equation (3). The manifold 701 defining the location of the catheter tip 377 relative to the fiduciary markers 700Ax-700Bx is therefore the difference between vector function $f_i$ to vector function $g_i$ relative to the angle and mapped over time domain T, where T is $\{t_1, t_2 \ldots t_n\}$. In summary, the methodology of synchronizing the catheter tip 377 position relative to the stereotactic framing formed by the fiduciary markers 700Ax through 700Bx allow the GCI controller 501 to provide first a closed servo loop modality whereby the surgeon can set the desired position (DP=$P_2$) relative to actual position (AP=$P_1$) while the machine performs the necessary arithmetical calculations along the "C" curve 985. Second, the optimal power setting is generated by the electromagnet clusters 920 and 930 with respect to the distance r 971, and angle Φ 984, relative to the catheter tip 377.

FIG. 5B shows the use of the apparatus described in FIG. 5A while performing a pacemaker electrode implantation. FIG. 5B further illustrates the implantation of cardiac pacemaker 801 with electrodes as shown, placed in an area relative to the S.A. Node 802, A.V. Node 803, and a bundle of His 804. Further illustrated are the right and left bundle branches 805. Pacemaker implantation is essential for the survival of patients with heart rhythm or electrical conduction disturbances. This procedure is performed by the implantation of a small electrode in the heart cavity wall (ventricle or atrium). The other end of the electrode is attached to an electronic device 801 which is implanted under the chest skin and which generates stimulation pulses to simulate the heart rhythm. Similar devices apply electrical shock when life threatening heart electrical disturbances are detected by the electrodes Automatic Implantable Cardiac Defibrillator (AICD). These electrodes are placed through a vein by pushing and manipulating under fluoroscopy. Through the use of the apparatus GCI 501, guidewire 379 fitted with magnetic tip 381 is used to carry and place the electrodes of pacemaker 801 in their proper position by using the CGI system. With the fiduciary markers 700A1, 700A2, 700A3, 700A4, 700B1, 700B2, 700B3, and 700B4 in place, the physician navigates the guidewire 379 through the heart lumen while having a continuous dynamic referential frame identifying the guidewire tip 381 using the position data from radar 1000 and the employment of the 6-DOF sensor 2000 as shown in FIG. 5 and further illustrated by FIG. 5A. Often the manipulation to place the electrodes in the proper position is difficult and the results are sub-optimal due to anatomical variations. The use of the controller 501 provides simplicity in performing such a complex operation while the physician is capable of moving, pushing, and placing the electrodes of pacemaker 801 in its desired anatomical position without compromise due to the inability of navigating, guiding, controlling, and imaging the movement of the guidewire and the pacemaker electrodes accurately.

FIG. 6 and 6A are perspective views of a catheter assembly 375 and a guidewire assembly 379 for use with the GCI system 503. The catheter assembly 375 is a tubular tool that includes a catheter body 376 which extends into a flexible section 378 that possesses increased flexibility for allowing a more rigid responsive tip 377 to be accurately steered through a torturous path. The magnetic catheter assembly 375 in combination with the GCI apparatus 501 reduces or eliminates the need for the plethora of shapes normally needed to perform diagnostic and therapeutic procedures. This is due to the fact that during a conventional catheterization procedure the surgeon often encounters difficulty in guiding a conventional catheter to the desired position, since the process is labor intensive and relies on manual dexterity to maneuver the catheter through a tortuous path of, for example, the cardiovascular system. Thus, a plethora of catheters in varying sizes and shapes are made available to the surgeon in order to assist him/her in the task, since such tasks require different bends in different situations due to natural anatomical variations within and between patients. By using the GCI apparatus 501, only a single catheter is needed for most, if not all patients, because the catheterization procedure is now achieved with the help of an electromechanical system that guides the magnetic catheter and guidewire assembly 375 and/or 379 to the desired position within the patient's body 390 as dictated by the surgeon's manipulation of the virtual tip 405, without relying on the surgeon pushing the catheter quasi-blindly into the patient's body 390. The magnetic catheter and guidewire assembly 375, 379 provides the flexibility needed to overcome tortuous paths.

The guidewire assembly 379 includes guidewire body 380 and a flexible section 382, which possesses increased flexibility for allowing a more rigid responsive tip 381 to be accurately steered around sharp bends so as to navigate a torturous path. The responsive tips 377 and 381 of both the catheter assembly 375 and the guidewire assembly 379 respectively, include magnetic elements such as permanent magnets. The tips 377 and 381 include permanent magnets that respond to the external flux generated by the upper electromagnetic cluster 920 and the lower electromagnetic cluster 930.

The tip 377 of the catheter assembly 375 is tubular, and the responsive tip 381 of the guidewire assembly 379 is a solid cylinder. The responsive tip 377 of the catheter assembly 375 is a dipole with longitudinal polar orientation created by the two ends of the magnetic element positioned longitudinally within it. The responsive tip 381 of guidewire assembly 379 is a dipole with longitudinal polar orientation created by the two ends of the magnetic element 377 positioned longitudinally within it. These longitudinal dipoles allow the manipulation of both responsive tips 377 and 381 with the GCI apparatus 501, as the upper electromagnetic cluster 920 and the lower electromagnetic cluster 930 will act on the tips 377 and 381 and "drag" them in unison to a desired position as dictated by the operator.

FIG. 6B is a representation of a catheter fitted with a magnetic tip and two piezoelectric rings. FIG. 6B further illustrates an added improvement of the catheter assembly 375 and guide-wire assembly 379 to be used with the GCI system 503, with the exception that catheter assembly 953 is fitted with an additional two piezoelectric rings or polymer of semi-conducting properties, 951 and 952, located as shown. The radar system 950 in combination with the controller 501 provides an additional detection modality of the catheter tip whereby an RF signal is emitted so as to excite the two piezoelectric rings or the polymer and thus provide a measure of rotation of the catheter tip relative to the north pole of the magnet 377. The GCI system 503 can define the angle of rotation of the tip 377 and in a more elaborate scheme known to those familiar with the art the piezoelectric rings or polymer 951, 952, can provide additional position information to define the position, orientation, and rotation of the catheter tip 377 relative to the stereotactic framing 701 as described in FIGS. 5, 5A, and 5B.

Figure 7:
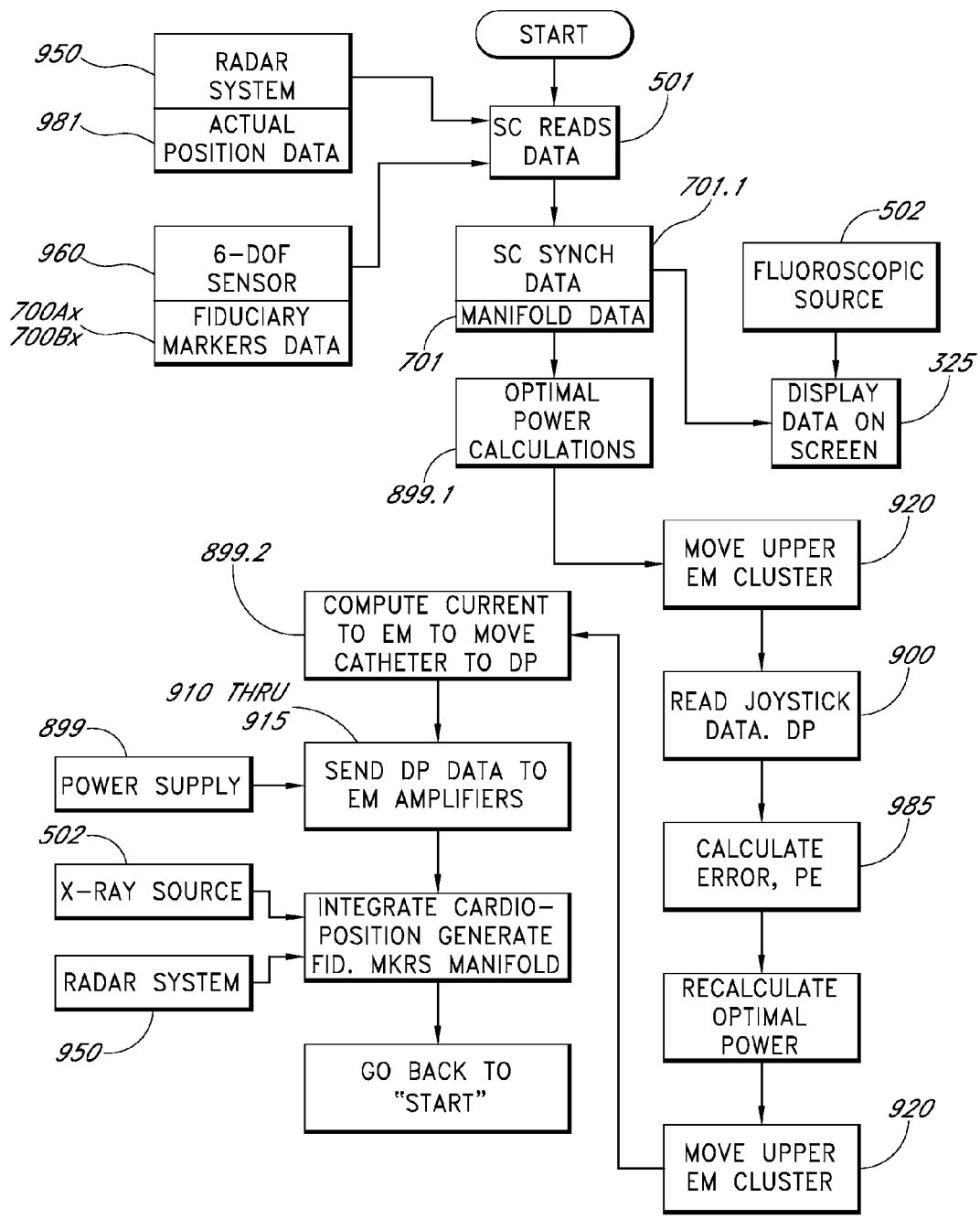
FIG. 7 is a graphical representation of the computational and a logical flow of the GCI system that includes the radar system and the 6-DOF sensor.

FIG. 7 illustrates a logical computational flow performed by the system controller (SC) 501 for determining the position of the actual catheter tip (AP) 377. The controller also combines catheter tip position data (measured by the radar system 950) with the fiduciary markers position data (measured by the 6-DOF sensor 960) to determine the position of the catheter tip in the body of the patient and to synchronize the catheter position with image data (if available).

1. The controller 501 inhibits the outputs of the X-axis controller and amplifier (XCA) 911 and 910, the Y-axis controller and amplifier (YCA) 913 and 912, and the Z-axis controller and amplifier (ZCA) 915 and 914.
2. The controller 501 reads data from the radar system 950, identifying the actual position (AP) 981 of the catheter tip 377.
3. The controller 501 reads data from the user input devices 900 for a new desired position (DP) 982 of the catheter tip as directed by the surgeon.
4. The controller 501 performs the mathematical solution for the "C" curve 985.
5. The controller 501 reads the data from the 6-DOF sensor, denoting the position of the fiduciary markers 700Ax, 700Bx which form the stereotactic frame.
6. The controller 501 obtains digital image data 702 from the image source 502.
7. The controller 501 synchronizes the data from of the catheter tip position 377 with the data obtained from the 6-DOF sensor and arranges the combined data in the form of a manifold 701.
8. The controller 501 superimposes the manifold 701 onto the digital image obtained from the image source 702.
9. The controller 501 computes the optimal distance r 971 and the angle Φ 984 of the electromagnet clusters 920 and 930, thereby providing for optimal power setting of the electromagnet clusters 920 and 930 relative to the position of the patient 390.
10. The controller 501 repeats steps 1 through 9 above as necessary.
11. The controller 501 calculates an error position (PE) 983 which is the difference between the actual position (AP) 981 and the desired position (DP) 982 of the catheter tip 377, also denoted as curve "C" 985 in FIG. 2L and represented by expression (PE=[AP−DP]).
12. The controller 501 repeats the process of optimal power setting algorithm so as to afford a geometry which accommodates the travel between the actual position of the catheter tip 377 and the desired position of the tip set by the surgeon.

13. The GCI controller 501 commands the upper electromagnet cluster 920, using the motorized gimbaled and computer controlled apparatus 970, to move in such a manner so as to obtain an optimal configuration for the electromagnet system.

14. The controller 501 inputs the corrected magnetic field data as described by the procedure identified by FIGS. 2C through 2H to the X-axis controller and amplifier (XCA) 911 and 910, the Y-axis controller and amplifier (YCA) 913 and 912, and the Z-axis controller and amplifier (ZCA) 915 and 914, and interpolates a 5-axis data set from the three orthogonal components (Bx, By, Bz) of the magnetic field B produced on the actual tip 377.

15. The controller 501 sends the new desired position data (DP) 982 corresponding to new desired co-ordinates to the X-axis controller and amplifier (XCA) 911 and 910, the Y-axis controller and amplifier (YCA) 913 and 912, and the Z-axis controller and amplifier (ZCA) 915 and 914, so as to set the appropriate current in the coils 901 through 906.

16. The controller 501 further integrates the cardio position (CP) from the image souce 702 and the radar system 950 including, for example, gating data from an electrocardiogram (EKG) 502 and the stereotactic frame formed by the fiduciary markers 700Ax through 700Bx, so as to dynamically link the various inputs of cardio position, actual catheter tip position (AP) 981 and the fiduciary markers as a manifold 701. Data such as the cardio position (CP) and the pulmonary data set are dynamic and time-variant due to the beating of the heart and the pulmonary motion of the lungs.

17. The controller 501 repeats the above process as needed.

The controller 501 sends feedback data to the Virtual Tip (VT) 405 to provide tactile feedback if the position error (PE) 983 exceeds a predetermined amount in a predetermined time in any axis or axes, thereby notifying the operator of an obstruction encountered by the catheter tip 377. It is assumed that if the (PE) 983 is not eliminated by the normal operation of the GCI apparatus 501 within an expected amount of time or cycles of steps 1 through 14 above, then an obstacle is likely to have been encountered by the actual catheter tip 377. This is perceived by the operator through tactile feedback generated by a resistance on the stick and acting on one or more of the user input devices 900 such as the virtual tip 405.

Figure 8:
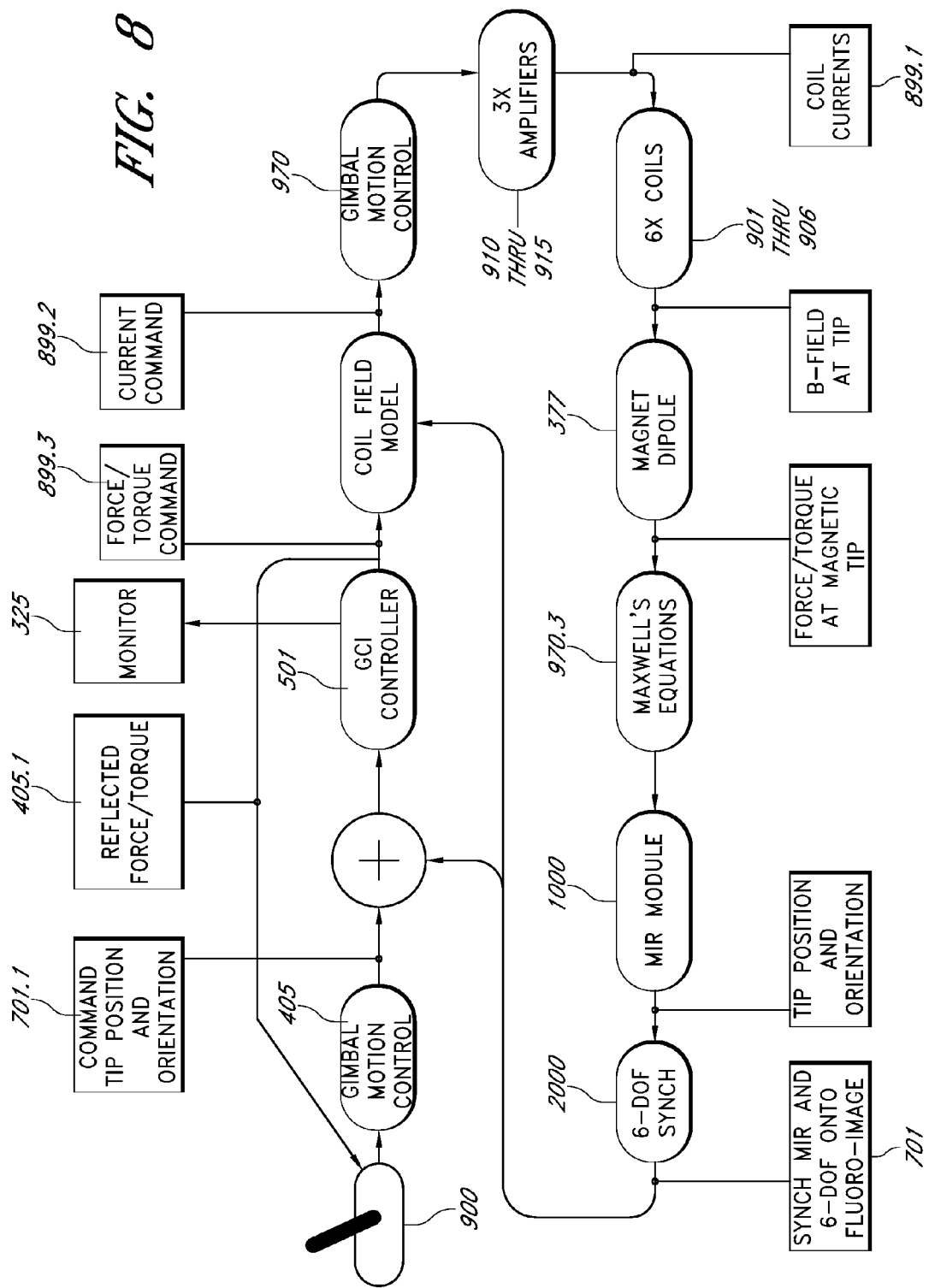
FIG. 8 is a functional block diagram of the signal flow in the CGCI apparatus.

FIG. 8 is a functional block diagram of the signal flow in the CGCI apparatus. The figure illustrates the operation of the virtual tip 405, which provides intuitive joystick-type control of the catheter tip by the surgeon. The surgeon pushes, pulls, or rotates the virtual tip 405 in the desired direction so as to cause a similar movement of the catheter tip 377 within the patient's body 390. If an obstruction is encountered by the catheter tip 377, the virtual tip 405 responds with tactile feedback in the form of resistance to movement in the appropriate axis or axes. Thus the surgeon can "feel" the actual tip as it is advancing. When tip 405 is released, the catheter tip 377 is forcefully held in its current position. System Controller of GCI 501 correlates the actual tip position (AP) 981 with cardio-position data (CP) obtained from the manifold 701 and generated by the radar 950 and the 6-DOF sensor 960. These data sets are superimposed on fluoroscopic image 702 generated by auxiliary equipment 502, and displayed on monitor 325 with the combined and synchronized tip and X-ray imagery formed as manifold 701. The display of the three-dimensional actual tip position (AP) 981 is continuously updated on a real-time basis with the AP data. Relatively fewer frames of X-ray imagery are used to overlay the display with CP data. This correlation of AP and CP data is possible because the X-ray and the radar data presented in the 701 synthetic image have a common reference point namely the fiduciary markers, 700Ax through 700Bx, (i.e., both are stationary relative to the beating heart). Thus the present technique significantly reduces X-ray exposure to the patient and staff while providing a superior method of observing the heart and catheter tip 377.

FIG. 8 further describes the operation of the GCI apparatus 501 by showing the procedure wherein the hand motion of the surgeon operating the user input devices 900 (such as the virtual tip 405) is captured and translated into movement command. An optimization of the power versus force required to move the catheter tip 377 while using the amplifiers 910 through 915 to generate the necessary currents for the coils 901 through 906 is provided. The coils produce a B field at the tip of catheter 377, responding to the force/torque generated at the tip 377 according to Maxwell's equations. The movement of the catheter tip 377 is monitored in real time by the radar system 950, where tip position and orientation information are displayed through a process of synchronization 701 using the fiduciary markers 700Ax through 700Bx through the use of the 6-DOF sensor 2000, thereby gating the position as well as the reflected force/torque generated by the actual tip. This process continuously repeats itself so as to respond to the operator's movement by the use of the user input devices 900. The above procedure noted by FIG. 8 is clear and intuitive to those familiar with the art and is further detailed in FIGS. 1 through 7.

As shown in FIG. 4, the process is described as follows: i) the operator adjusts the physical position of the virtual catheter tip 405 to a desired position, ii) a change in the virtual tip 405 position is encoded in the controller 501, producing new position data from the radar 950 which too is received at the controller 501, iii) the controller 501 generates commands sent to a servo system control module, iv) the servo system control module controls the gimbal and motion control apparatus 970 to adjust the position of the coils 901 through 906 to optimizing the position of the electromagnet clusters 920 relative to 930, by varying the distance r 971, and the angle Φ 984 of the electromagnet clusters, v) current is sent to the coils 901-906 causing the position of the actual magnetic catheter tip 377 within the patient's body 390 to change, vi) the new position of the actual catheter tip (AP) is then sensed by the radar system 950 and the 6-DOF sensor 960, and the catheter position is superimposed on the image produced by fluoroscopy and/or other imaging modality 702, and vii) feedback is provided to the servo system control apparatus and the monitoring system 501 of the operator interface.

FIG. 9 shows the arrangement of electromagnetic coils 132X, 132Y, 132Z, 138X, 138Y, and 138Z in a polar configuration, 374 that illustrates the use the GCI apparatus 503 with an alternate magnet system using a bi-plane X-ray support mechanism, as opposed to the arrangement noted in FIG. 2 as the "C"-arm 391 layout. FIG. 9 further illustrates the overall relationship between the elements comprising the GCI apparatus 501, which includes an operating table 389, the patient 390, a T-axis encoder 394, a trunnion 388, a support assembly 385, a polar support 391.1, a G-axis encoder 393, the X-ray source 383, and an image intensifier 384. This overall arrangement is referred to as polar configuration 374, and is contrasted with the "C"-arm approach 391 where the electromagnets 901 through 906 are configured as part of a toroid in a cluster 920, 930. The architecture shown in FIGS. 2, 2A, and 2B, is advantageous as the strength of the electromagnetic field B increases towards the center line of the gap, and the gradient peaks at the edge of the gap, enabling the GCI 501 to form a lobed magnetic field structure which is not as easily obtainable by the use of the Bi-plane axio-symmetric layout noted in FIG. 9. The GCI 501 incorporates such an arrangement so as to provide the benefits of pushing, pulling and guiding the magnetically coupled catheter tip 377 in a polar configuration such as the one noted in FIG. 9.

In employing the polar configuration 374 the apparatus uses a T-axis encoder 394 and the G-axis encoder 393 which provide the system with gantry position information for use in calculating the required coordinate rotation prior to energizing the electromagnets. The polar configuration 374 uses the trunnion 388 which acts as a truss for the support assembly 385. Polar support 391.1 pivots on the G-axis of support assembly 385, and the polar assembly 391.1 supports the X-ray source 383 and X-ray image intensifier 384 which produce the X-ray images that are superimposed together with the actual catheter tip position on the monitor 325. Polar support 391.1 provides a mounting surface for electromagnets 132X, 132Y, 132Z, 138X, 138Y, and 138Z in their appropriate coaxial arrangements.

The trunnion 388 is centered on the T-axis 387. The T-axis encoder 394 is mechanically coupled to the trunnion 388 in order to encode positional data of the support assembly 385 in the T-axis. A gimbal-axis (G-axis) 386 intersects with the T-axis 378 at the center point of the polar support 391.1. This center point coincides with the center point of the X-ray field of view. A G-axis encoder 393 is mechanically coupled to the support assembly 385 along the G-axis 386.

The 6-DOF sensor provides the sensing of six degrees of freedom (DOF) relative to the fiduciary markers. It accomplishes this by emitting a laser beam and detecting the reflection off the markers. Inside the sensor, the beam is split and directed onto three photo diodes. The analog signals from the diodes are digitized and fed into a computer which can instruct corrective action for a machine or output position readings.

Figure 10:
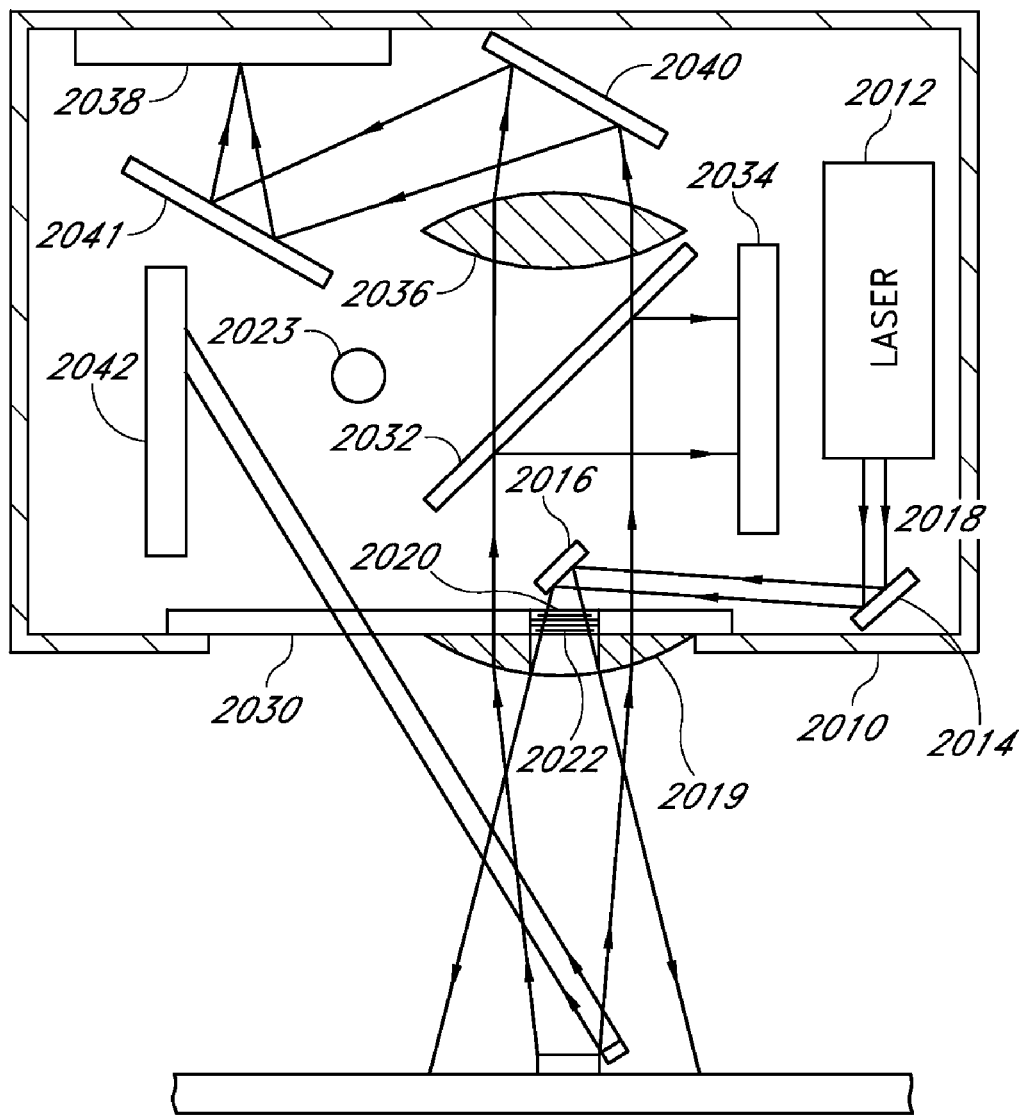
FIG. 10 shows one embodiment of the 6-DOF sensor.

FIG. 10 shows the 6-DOF sensor wherein a laser source 2012 illuminates mirrors 2014, 2016 to guide a beam 2018 to the primary optical axis of the sensor. The beam is passed through two negative lenses (2020 and 2022) which diverge the beam. In one embodiment, the divergence angle is approximately 0.3 radians (half angle) to produce 1 cm diameter laser spot at about 3.5 cm from the face of the sensor. Other divergence angles can be used as well. The sensor's field of view can be changed by choosing different negative lenses 2020, 2022 which in turn change the divergence angle and spot size at a given distance.

Two reflective reference markers, e.g., a 4 mm diameter dot 2024 and a 1×1 mm bar 2026, are mounted on non-reflective tape and applied to the patient. The laser light reflects off the markers and back into the sensor. Because the beam is diverging, the reflections are magnified in area when the light returns to the sensor, allowing most of the light to go around the small negative lenses and through a relatively large positive lens instead. Lens 2019 has a hole in its center to pass the outgoing beam 2018, but has a focal length which collimates the diverging reflection beam. In other words, the positive focal length off lens 2019 is the same as the negative focal length of the lenses 2020 and 2022 by bending the diverging rays of reflected light from the dot 2024 to enter the sensor in parallel when the dot is located around half that focal length from the sensor. As the collimated reflection beam continues to propagate into the sensor it passes a band pass filter 2030. The filter 2030 passes the laser light but blocks light at other wavelengths. Inside the sensor, light from the dot 2024 is divided into two beams by a beam splitter 2032. Half of the beam is reflected 90 degrees into lateral effect photo diode 2034. The other half of the beam passes through the beam splitter, into a positive lens 2036, off mirrors 2040 and 2041, and onto another photo diode 2038.

Light from bar 26 also passes through the filter 2030. However, because reflective bar 2026 is tilted relative to the dot, the laser light that reflects from it is at a greater angle of divergence. The greater angle of reflection causes the light to pass through a different location of the filter 2030, missing lens 2019 and the beam splitter and illuminating photo diode. To reduce the sensor's sensitivity to external light sources other than the laser, a light emitting diode 2023 can be installed inside the sensor to provide controlled background light.

Each of the three photo diodes (2034, 2038 and 2042) has different sensitivity to the relative position of the sensor and the reflectors (2024 and 2026), permitting any change in position in any of the six degrees of freedom to be delineated when decoupling in software. The photo diode 2042 is sensitive to translation between the bar 2026 and the sensor (Tz) and the rotation of the sensor about the axis normal to the surface (Rz) of dot 2024. The bar 2026 is tilted such that its reflection illuminates the center of photo diode 2042 if the sensor is at a prescribed stand-off distance from the bar 2026 (half the focal length of 2019). Therefore, any up-down deviation of the bar's reflection from the center of photo diode 2042 can be calculated as a distance of the sensor from the bar (Tz). Likewise, the radial location of the bar relative to the center of the dot is used as a reference for rotation about Rz. Consequently, right-left deviation of the bar's reflection from the center of photo diode 2042 can be calculated as rotation of the sensor about the normal axis of the dot (Rz).

In contrast, photo diode 2038 is most sensitive to tilt about the X and Y axis (Rx, Ry) as explained below. Because the laser beam is diverging as it strikes the reflective reference marker 2024, the reflected beam returns larger but on center with the negative lenses 2014, 2016 even when the sensor is tilted about the negative lenses, i.e., the return light enters the sensor perpendicular to the surface of the reference dot, regardless of sensor tilt. Although the light returns as before the tilt, the position of photo diode 2038 does change with tilt of the sensor. Consequently, during tilt, motion of photo diode 2038 relative to an unchanged focus of the reflected light provides sensitivity to tilt about the X and Y axis (Rx, Ry). Because of the nature of lenses, diode 2038 is not sensitive to pure translations of the reflector 2024 because a lens focuses all parallel rays passing through it to the same point, regardless of where the ray comes from, i.e., regardless of where the marker is translated.

In the case of photo diode 2034, the beam splitter 2032 reflects the light onto it without a lens in the path. Consequently, unlike diode 2038, diode 2034 is sensitive to lateral translation of the sensor relative to the reference dot (Tx, Ty). Photo diode 34 is also sensitive to tilt; however, this effect can be canceled in software using information from photo diode 38. Likewise, any coupling of photo diodes 42 with the other two photo diodes can be canceled in software.

The analog data from the diodes are digitized with an Analog to Digital converter and provided to a computer for processing as two channels from each of the three photo diodes. In this form, the data does not represent pure motions about the six axes because all but two of the channels have information on more than one motion, i.e. the channels are coupled. The information can be decoupled into pure measurements of motion about all six degrees of freedom. This decoupling is possible because each photo diode provides different information. Photo diode 38 is sensitive only to tilt about the X and Y axis (Rx and Ry). Therefore, the voltage readings from these channels represent pure tilt in those axes without sensitivity (coupling) to other motions. In contrast, photo diode 34 is sensitive to four axes of motion, rotation and translation about X and Y (Tx, Ty, Rx & Ry). However, by subtracting any voltage reading from the photo diode 38, the tilt sensitivity of photo diode 34 is negated, and the remaining voltage is representative of only translation about X and Y (Tx, Ty). Likewise, photo diode 42 is sensitive to all six degrees of freedom. But, by subtracting the voltage from the other two photo diodes, the remaining voltage is representative of only rotation and translation about the Z axis (Tz, Rz).

After all six channels are decoupled, the data can be displayed to the operator and/or provided to the CGI system.

The Six DOF sensor is capable of tracking all 6 degrees of freedom. Because the laser beam diverges, reflections from the markers are magnified on the photo diodes, increasing accuracy. This benefit, combined with high-resolution A to D converters provides micron accuracy in detecting translation and milliradian accuracy in detecting orientation. With different optics, field of view can be reduced to improve accuracy and visa versa. The markers conform to the contour of the body, so positioning the reflective markers (references) on the body is a 3-DOF task (Tx, Ty, Rz) that can be performed by the operator or a simple 3-axis computer-controlled machine. The 6-D)F sensor is non-contact and non-surface dependent As an optical sensor, it does not physically contact the body. The 6-DOF sensor uses lateral-effect photo diodes rather than a camera. Since photo diodes are smaller than a camera, the 6-DOF sensor is relatively smaller than a camera-based system.

Figure 11:
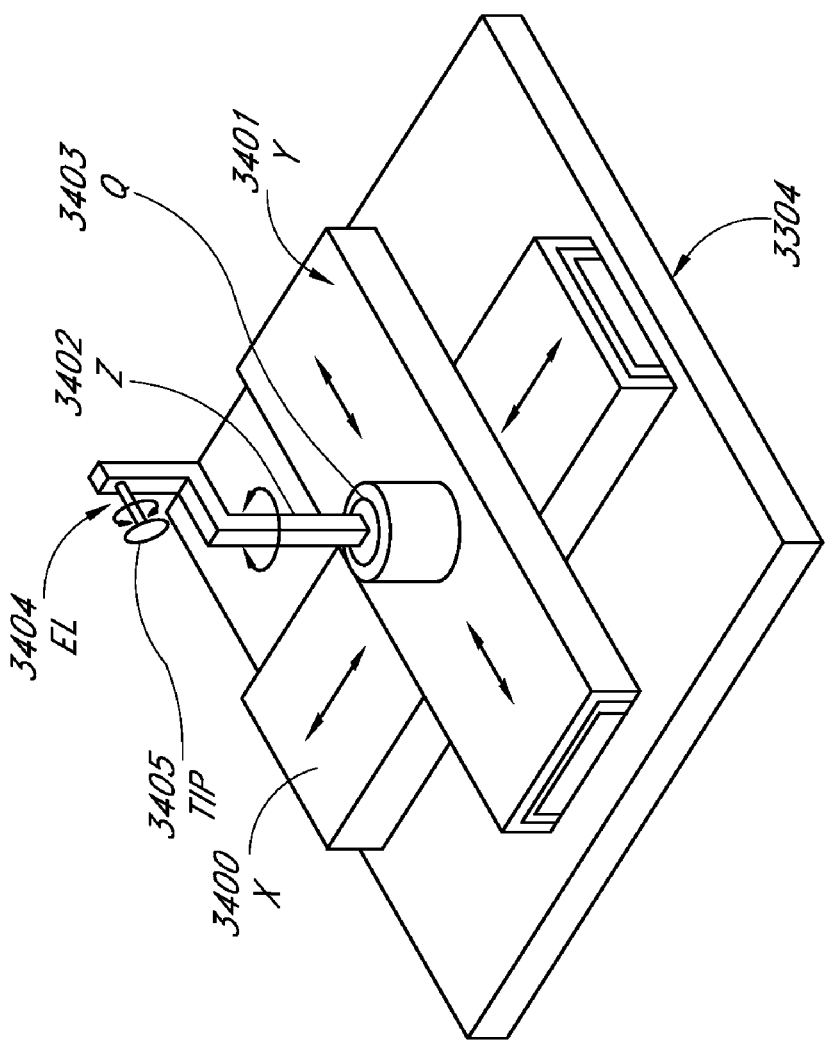
FIG. 11 is a perspective view showing capabilities of the Virtual Tip user input device.

FIG. 11 is a perspective view showing capabilities of the Virtual Tip user input device 405. The Virtual Tip 405 is a multi-axis joystick-type device that allows the surgeon to provide inputs to control the position, orientation, and rotation of the catheter tip 377. The Virtual Tip 405 includes an X input 3400, a Y input 3404, Z input 3402, and a phi rotation input 3403 for controlling the position of the catheter tip. The Virtual Tip 405 further includes a tip rotation input 3405 and a tip elevation input 3404. As described above, the surgeon manipulates the Virtual Tip 405 and the Virtual Tip 405 communicates the surgeon's movements to the controller 501. The controller 501 then generates currents in the coils to effect motion of the actual catheter tip 377 to cause the actual catheter tip 377 to follow the motions of the Virtual Tip 405. In one embodiment, the Virtual Tip 405 includes various motors and/or actuators (e.g., permanent-magnet motors/actuators, stepper motors, linear motors, piezoelectric motors, linear actuators, etc.) to provide force feedback to the operator to provide tactile indications that the catheter tip 377 has encountered an obstruction or obstacle.

Although the preceding description contains much specificity, this should not be construed as limiting the scope of the invention, but as merely providing illustrations of embodiments thereof. Thus, for example, the sensor that senses the position of fiduciary markers (reference markers) is described in embodiments as a 6-DOF sensor. One of ordinary skill in the art will recognize that other optical sensors that can sense the location of a reference marker (e.g., a camera) can be used as well. Moreover, non-optical sensors such as radar, ultrasonic sensors, and the like can be used to detect the position of the fiduciary markers. In one embodiment, the radar system 950 can be used in place of the 6-DOF sensor 960 to detect radar-reflective fiduciary markers.

Many other variations are possible within the scope of the present invention. For example, the modulation of the electromagnets can be controlled in such a way as to cause a vibratory or pulsating motion of the tip to aid in crossing plaque. The responsive tip(s) can be electromagnetic rather than permanent magnets. The magnetic field external to the body can be generated by a permanent magnet or magnets. The control of the external magnetic field can be accomplished by manually administering the field generating devices. AC induction with its associated magnetic effects can be used by causing a coil or coils wound around the tip to respond to an impressed time variant field. Materials with Curie temperatures within a few degrees of body temperature can be used as magnetic flux switches for selective tip control by irrigating them with fluids having appropriate temperatures; electrostatic phenomena can enhance magnetic effects. Artificial intelligence can replace the operator control for producing command inputs; an expert system can replace or augment operator inputs. The apparatus can be used to incubate various body cavities and organs other than the heart. The apparatus can be used for human and animal procedures such as egg harvesting and embryo implantation. The responsive tip can be attached to a coherent fiber optic bundle to provide viewing of internal structures with unprecedented maneuverability, Internal radioisotope therapy can be precisely performed by delivering a palletized source directly to a tumor using a guided catheter. Internal tissue samples can be obtained without major surgery; a fiber optic light guide equipped with a responsive tip can be accurately positioned to deliver laser light to a specific internal location without major surgery. Thus, the scope of the invention is limited only by the claims.

What is claimed is:

1. A method for controlling movement of a tool having a distal end to be inserted in a body, comprising;
    applying a force to said distal end of a tool inserted in a body by generating an external magnetic field;
    regulating said force to move said distal end in a desired direction within said body; and
    locating said distal end in said body by radar by processing radar data to identify contrast between said distal end and body tissues near said distal end, said contrast resulting from the dielectric constants of said distal end and said body tissues wherein said processing of said radar data filters out the background clutter associated with said body tissues based on said dielectric constants to determine the position coordinates of said distal end.

2. The method of claim 1, further comprising changing a visual representation of said distal end in substantially real time as said distal end moves through the body.

3. The method of claim 1, further comprising controlling one or more electromagnets to produce said external magnetic field.

4. The method of claim 1, further comprising locating a plurality of fiduciary markers and synchronizing said markers with positions on a real-time image of at least a portion of the body.

5. The method of claim 1, further comprising determining a current position of said distal end in comparison to a desired location.

6. The method of claim 1, wherein determining said current position of said tool distal end comprises:

inputting a dynamic cardio-position via said controller; and calculating said current position as a function of said cardio-position.

7. The method of claim 1, further comprising computing a position error of said distal end.

8. The method of claim 7, further comprising altering at least one of a duty cycle and a polarity of modulation inputs to at least one of said X-axis controller, said Y-axis controller, and said Z-axis controller when said position error is greater than a specified minimum value.

9. The method of claim 7, further comprising producing a tactile feedback if said position error exceeds a predetermined amount along at least one axis.

10. The method of claim 7, wherein said system controller causes said tool distal end to move so that its position corresponds to position data from a Virtual Tip.

* * * * *